(12) United States Patent
Goto et al.

(10) Patent No.: US 6,825,310 B2
(45) Date of Patent: Nov. 30, 2004

(54) HALOGENATED AROMATIC COMPOUND, POLYMER THEREOF, AND PROTON-CONDUCTIVE MEMBRANE COMPRISING SAME

(75) Inventors: Kohei Goto, Ibaraki (JP); Masayuki Takahashi, Ibaraki (JP); Yoshitaka Yamakawa, Ibaraki (JP); Makoto Higami, Ibaraki (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 10/105,213

(22) Filed: Mar. 26, 2002

(65) Prior Publication Data

US 2002/0188097 A1 Dec. 12, 2002

(30) Foreign Application Priority Data

| Mar. 30, 2001 | (JP) | 2001-101586 |
| Jul. 30, 2001 | (JP) | 2001-230650 |
| Sep. 28, 2001 | (JP) | 2001-303964 |

(51) Int. Cl.$^7$ .............................................. C08G 65/38
(52) U.S. Cl. ....................... 528/86; 528/125; 528/127; 528/391; 528/397
(58) Field of Search ........................ 528/86, 125, 127, 528/390, 397

(56) References Cited

U.S. PATENT DOCUMENTS

| 6,084,053 A | 7/2000 | Matsubara et al. |
| 6,300,465 B1 | 10/2001 | Akiike et al. |
| 6,555,626 B2 | 4/2003 | Goto et al. |

FOREIGN PATENT DOCUMENTS

| EP | 0 317 226 | 5/1989 |
| EP | 1 138 712 | 10/2001 |
| GB | 1 286 673 | 8/1972 |
| WO | WO 00/51716 | 9/2000 |

OTHER PUBLICATIONS

Derwent Search Result of patent family search of EP 1138712/pn.
Derwent Publications, AN 1989:440841, XP-002204442, CN 87 100 641, Aug. 17,1988.
M. Shibata, et al., Macromol. Chem. Phys., vol. 197, No. 10, pp. 3297-3308, XP-001074022, Molecular Structure of Some Model Compunds for Poly(Aryl Ether Ketone)s, 1996.
H. Colquhoun, et al., Organic Letters, vol. 3, No. 25, pp. 4031-4034, XP-002204441, "Synthesis and Ring-Expanding Oligomerization of an Extremely Strained Macrocyclic Aromatic Ether-Sulfone", 2001.

*Primary Examiner*—Duc Truong
(74) *Attorney, Agent, or Firm*—Oblon, Spivak, McClelland, Maier & Neustadt, P.C.

(57) ABSTRACT

A polymer which has a flexible structure in its main chain and thus exhibits a high toughness and can difficultly be deteriorated in its mechanical properties and thermal properties even when sulfonated, a sulfonic acid group-containing polymer obtained by the sulfonation of the polymer, and a proton-conductive membrane having an excellent mechanical strength and durability made of the sulfonic acid group-containing polymer. A novel halogenated aromatic compound represented by the following general formula (1m) is provided:

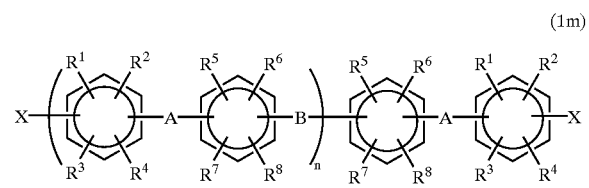

(1m)

wherein A independently represents an electron-withdrawing group; B independently represents an electron-donating atom or group; X represents a chlorine atom, iodine atom or bromine atom; $R^1$ to $R^8$ may be the same or different and each represent a hydrogen atom, fluorine atom or alkyl group; and n represents an integer of 2 or more.

10 Claims, 20 Drawing Sheets

HALOGENATED AROMATIC COMPOUND, POLYMER THEREOF, AND PROTON-CONDUCTIVE MEMBRANE COMPRISING SAME

FIELD OF THE INVENTION

The present invention relates to a novel halogenated aromatic compound, a polyphenylene polymer obtained by the polymerization of such a halogenated aromatic compound as a monomer component, and a proton-conductive membrane comprising a sulfonation product of such a polymer. It is known that a proton-conductive membrane can be used as a proton-conductive membrane for primary battery electrolyte, secondary battery electrolyte, fuel cell polymer solid electrolyte, display element, various sensors, signal transfer medium, solid capacitor, ion exchange membrane, etc.

DESCRIPTION OF THE RELATED ART

Electrolytes are usually used as (aqueous) solutions in many cases. In recent years, however, there is a growing tendency to replace such aqueous soluble-form electrolytes with solid electrolytes. The first reason for this is the easiness of processing in applications of solid electrolytes to, e.g., the electrical/electronic materials mentioned above. The second reason is the trend toward reduction in weight, thickness, length and size, and toward energy saving.

Conventional proton-conductive materials include both inorganic materials and organic materials. Examples of the inorganic materials include uranyl phosphates which form hydrate. However, these inorganic compounds are insufficient in interfacial contact to pose many problems concerning the formation of a conductive layer on a substrate or electrode.

On the other hand, examples of the organic compounds include organic polymers such as polymers belonging to the so-called cation-exchange resins, e.g., sulfonated vinyl polymers such as sulfonated polymers with perfluoroalkylsulfonic acid represented by Nafion (manufactured by E. I. Du Pont de Nemours & Co., Inc.), and perfluoroalkylcarboxylic acid polymers, and polymers prepared with incorporating sulfonic acid groups or phosphoric acid groups into heat-resistant polymers such as polybenzimidazole and poly(ether ether ketone)s [see *Polymer Preprints*, Japan, Vol. 42, No. 7, pp. 2490–2492 (1993); *Polymer Preprints*, Japan, Vol. 43, No. 3, pp. 735–736 (1994); and *Polymer Preprints*, Japan, Vol. 42, No. 3, p. 730 (1993)].

These organic polymers are usually used in the form of a membrane. A conductive membrane made of these organic polymers can be bonded to an electrode while taking advantage of the solvent solubility or thermoplasticity. However, many of these organic polymers have the following problems besides being still insufficient in proton conductivity. The organic polymers deteriorate in durability or in proton conductivity at elevated temperatures (100° C. or higher). When sulfonated, the organic polymers undergo embrittlement, deteriorate in mechanical strength and have a great dependence on humidity conditions. Further, the adhesion of the organic polymers to the electrode is not fully satisfactory. Moreover, the conductive membrane swells excessively during operation due to the hydrophilic polymer structure, and this swelling leads to a decrease in strength properties or a deformation. Consequently, application of those organic polymers to the aforementioned electrical/electronic materials and the like pose various problems.

U.S. Pat. No. 5,403,675 proposes a solid polymer electrolyte comprising a sulfonated rigid polyphenylene. This polymer is produced from a polymer comprising a phenylene chain obtained by polymerizing an aromatic compound (the polymer structure is described at column 9 in the patent specification) by reacting the phenylene polymer as the main component with a sulfonating agent to incorporate sulfonic acid groups thereinto. However, the incorporation of a large amount of sulfonic acid groups results in a sulfonated polymer having considerable deterioration in mechanical properties such as toughness (e.g., elongation at break, flexing resistance) and hot water resistance although proton conductivity improves with the increasing amount of sulfonic acid groups incorporated.

SUMMARY OF THE INVENTION

Accordingly one object of the invention is to provide a polymer which has a flexible structure in its main chain and thus exhibits a high toughness and can difficultly be deteriorated in its mechanical properties and thermal properties even when sulfonated.

Another object of the invention is to provide a sulfonic acid group-containing polymer obtained by the sulfonation of the polymer.

Still another object of the invention is to provide a proton-conductive membrane having an excellent mechanical strength and durability made of the sulfonic acid group-containing polymer.

The above objects of the invention will become apparent from the following detailed description and examples.

The invention provides a compound useful as a monomer effective for the incorporation of a flexible structure in a polymer. The compound is a halogenated aromatic compound represented by the following general formula (1m):

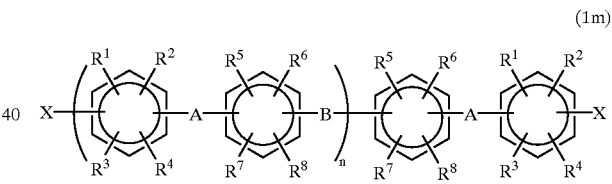

wherein A independently represents an electron-withdrawing group; B independently represents an electron-donating atom or group; X represents a chlorine atom, iodine atom or bromine atom; $R^1$ to $R^8$ may be the same or different and each represent a hydrogen atom, fluorine atom or alkyl group; and n represents an integer of 2 or more, preferably 2 to 100, more preferably 2 to 80.

The halogenated aromatic compound provides a polymer with a flexible structure to enhance the toughness of the polymer.

The invention also provides a polyphenylene polymer having a repeating unit represented by the following general formula (1):

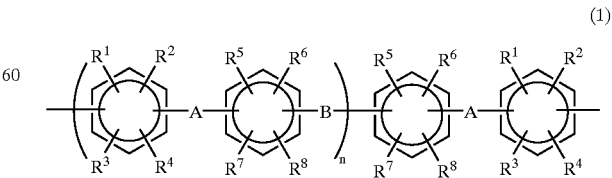

wherein A, B, $R^1$ to $R^8$, and n are the same as defined in above.

The polyphenylene polymer may be a homopolymer or a copolymer containing other repeating units.

The invention further provides a polyphenylene copolymer having a repeating unit represented by the general formula (1) and a repeating unit comprising other divalent aromatic groups.

The invention further provides as one of the foregoing copolymers a polyphenylene copolymer wherein the repeating unit comprising a divalent aromatic group is at least one unit selected from the group consisting of those represented by the following general formulae (2) to (5):

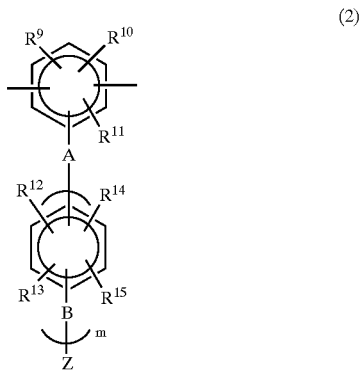

(2)

wherein A and B are the same as defined above; $R^9$ to $R^{15}$ may be the same or different and each represent a hydrogen atom or alkyl group; Z represents an aryl group; and m represents an integer of from 0 to 2;

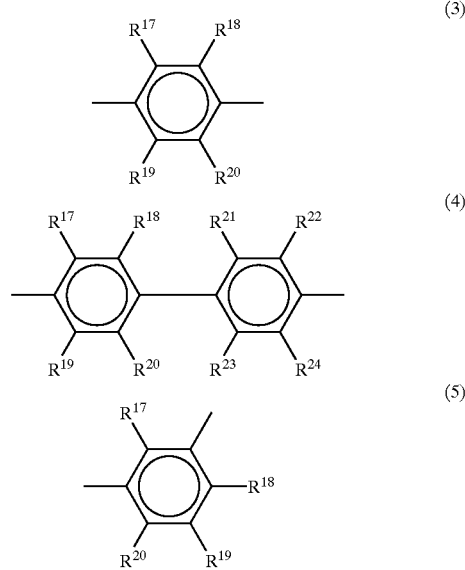

(3)

(4)

(5)

wherein $R^{17}$ to $R^{24}$ may be the same or different and each represent a hydrogen atom, fluorine atom, alkyl group or aryl group.

The polyphenylene copolymer can be easily sulfonated to provide proton conductivity.

The invention further provides the foregoing copolymer further containing a sulfonic acid group.

The sulfonic acid group-containing copolymer is useful as a material of proton-conductive membrane.

The invention further provides a proton-conductive membrane comprising the foregoing sulfonic acid group-containing copolymer.

BRIEF DESCRIPTION OF THE DRAWINGS

By way of example and to make the description more clear, reference is made to the accompanying drawings in which.

DETAILED DESCRIPTION OF THE INVENTION

Figure 1:
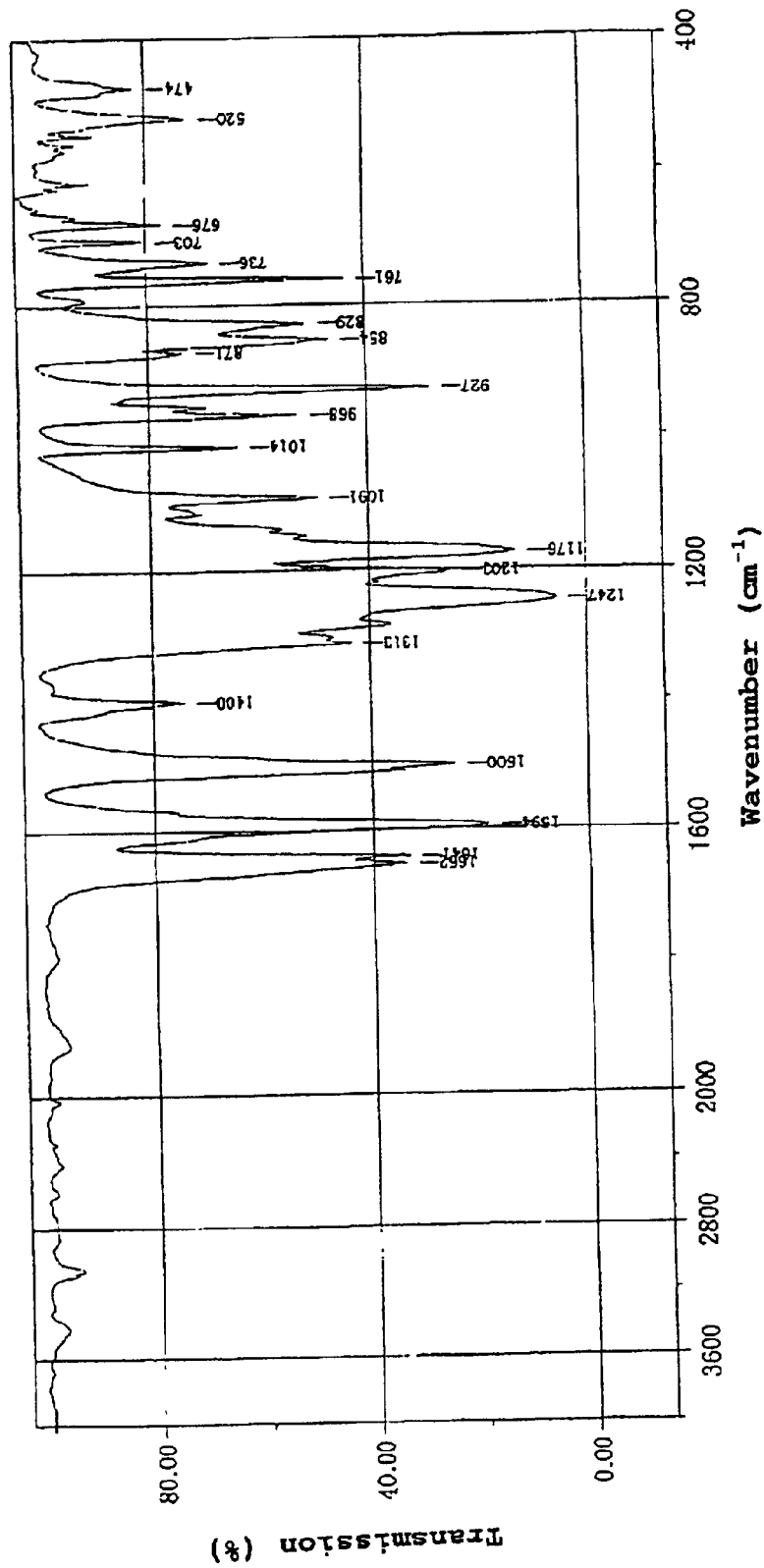
FIG. 1 is an IR spectrum of 2,2-bis[4-{4-(4-chlorobenzoyl)phenoxy}phenyl]-1,1,1,3,3,3-hexafluoroprop (BCPAF) as a halogenated aromatic compound of the invention obtained in Example 1.

The invention will be further described hereinafter.
Halogenated Aromatic Compound:

The halogenated aromatic compound of the invention represented by the general formula (1m) (hereinafter referred to as "monomer (1m)") provides a polymer with a flexible structure as a monomer unit to enhance the toughness and other mechanical strengths thereof.

The general formula (1m) will be further described hereinafter.

Examples of the group X include chlorine atom, bromine atom, and iodine atom.

A is an electron-withdrawing group such as —CO—, —CONH—, —(CF$_2$)$_p$— (in which p is an integer of from 1 to 10), —C(CF$_3$)$_2$—, —COO—, —SO— and —SO$_2$—. The term "electron-withdrawing group" as used herein is meant to indicate a group having a Hammett's substituent constant of not smaller than 0.6 or not smaller than 0.01 when located in the meta position or para position, respectively, in the phenyl group.

B is an electron-donating group or atom such as —O—, —S—, —CH=CH—, —C≡C—,

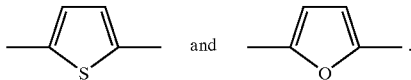

Examples of the monomer (1m) of the invention include 2,2-bis[4-{4-(4-chlorobenzoyl)phenoxy}phenyl]-1,1,1,3,3,3-hexafluoropropane, bis[4-{4-(4-chlorobenzoyl)phenoxy}phenyl]sulfone, and compounds represented by the following chemical formulae:

In order to convert a bisphenol having two phenols connected to each other with an electron-withdrawing group to a corresponding alkaline metal salt of bisphenol, an alkaline metal such as lithium, sodium and potassium, hydrogenated alkaline metal, hydroxidized alkaline metal, carbonate of alkaline metal or the like is added to the bisphenol in a polar solvent having a high dielectric constant such as N-methyl-2-pyrrolidone, N,N-dimethylacetamide, sulfolane, diphenylsulfone and dimethyl sulfoxide.

In general, the alkaline metal is reacted with the hydroxyl group of the phenol in some excess at the equivalence point. The alkaline metal is normally used in an amount of 1.1 times to twice the equivalent, preferably from 1.2 to 1.5 times the equivalent. During this procedure, the bisphenol is reacted with an aromatic dihalide compound activated by an electron-withdrawing group and substituted by a halogen atom such as fluorine and chlorine such as 4,4'-difluorobenzophenone, 4,4'-dichlorobenzophenone, 4,4'-chlorofluorobenzophenone, bis(4-chlorophenyl)sulfone, bis(4-fluorophenyl)sulfone, 4-fluorophenyl-4'-chlorophenylsulfone, bis(3-nitro-4-chlorophenyl)sulfone,

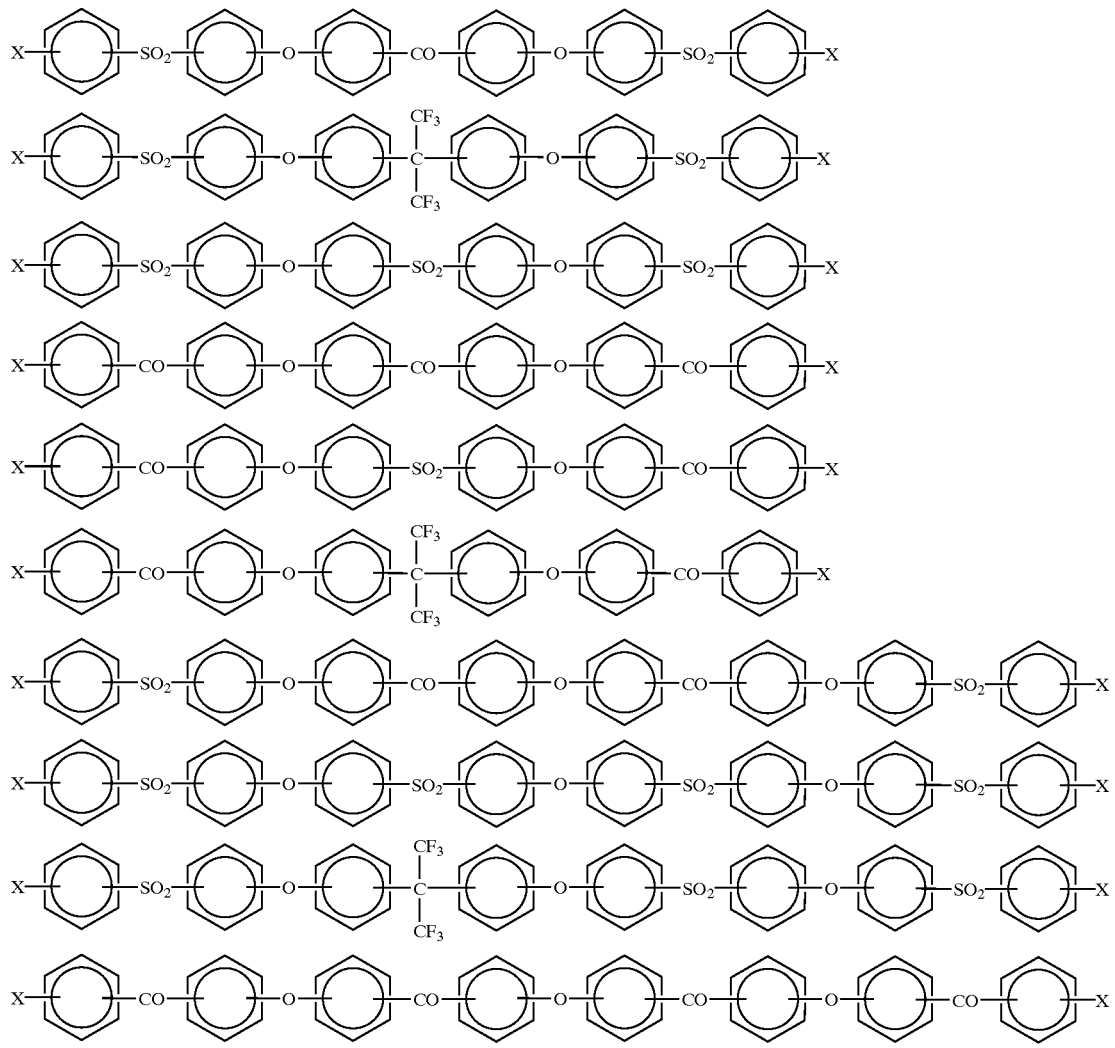

wherein X is the same as defined above.

The synthesis of the monomer (1m) can be accomplished by the following reaction.

2,6-dichlorobenzonitrile, 2,6-difluorobenzonitrile, hexafluorobenzene, decafluorobiphenyl, 2,5-difluorobenzophenone and 1,3-bis(4-chlorobenzoyl)

benzene in the presence of a solvent which forms an azeotrope with water such as benzene, toluene, xylene, hexane, cyclohexane, octane, chlorobenzene, dioxane, tetrahydrofurane, anisole and phenetole. From the standpoint of reactivity, a fluorine compound is preferred. However, taking into account the subsequent aromatic coupling reaction, it is necessary that the aromatic nucleophilic substitution reaction be designed such that the product is terminated by chlorine atom. The activated aromatic dihalide is used in an amount of from 2 to 4 mols, preferably from 2.2 to 2.8 mols per mol of the bisphenol. The bisphenol may be previously converted to an alkaline metal salt thereof prior to the aromatic nucleophilic substitution reaction. The reaction temperature is from 60° C. to 300° C., preferably from 80° C. to 250° C. The reaction time is from 15 minutes to 100 hours, preferably from 1 hour to 24 hours. In the most desirable method, as the activated aromatic dihalide represented by the general formula (6):

reaction, the polar solvent as mentioned above or the solvent which forms an azeotrope with water as mentioned above may be used. The bisphenoxy compound is then reacted with chlorobenzoyl chloride as an acylating agent in the presence of a Lewis acid Friedel-Crafts reaction activator such as aluminum chloride, boron trifluoride and zinc chloride. Chlorobenzoyl chloride is used in an amount of from 2 to 4 mols, preferably from 2.2 to 3 mols per mol of bisphenoxy compound. The Friedel-Crafts activator is used in an amount of from 1.1 to 2 mols per mol of activated halide compound such as chlorobenzoyl to be used as an acylating agent. The reaction time is from 15 minutes to 10 hours. The reaction temperature is from −20° C. to 80° C. As the solvent there may be used, e.g., chlorobenzene or nitrobenzene, which is inert to Friedel-Crafts reaction.

The monomer (1m) of the invention thus obtained can be identified for its structure by IR, NMR, elementary analysis, etc.

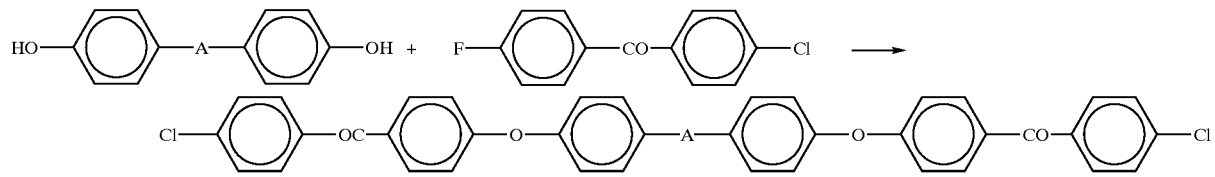

wherein A is as defined in the general formula (1m) there is used a chlorofluoro form having halogen atoms having different reactivities. In this manner, fluorine atom preferentially undergoes nucleophilic substitution reaction with the phenoxide to obtain the desired activated chlorine-terminated compound to advantage.

Alternatively, as described in Japanese Patent Laid-Open No. 1990-159, nucleophilic substitution reaction and electron-withdrawing substitution reaction may be combined to synthesize the desired flexible compound comprising an electron-withdrawing group and an electron-donating group.

In some detail, an aromatic bishalide activated by an electron-withdrawing group, e.g., bis(4-chlorophenyl) sulfone is allowed to undergo nucleophilic substitution reaction with phenol to produce a bisphenoxy-substituted compound. Subsequently, this substituted compound is allowed to undergo Friedel-Crafts reaction with 4-chlorobenzoyl chloride to obtain the desired compound. As the aromatic bishalide activated by an electron-withdrawing group there may be used the compound exemplified above. The phenol compound to be used herein may be substituted but is preferably unsubstituted from the standpoint of heat resistance or flexibility. For the substitution reaction of phenol, the phenol is preferably used in the form of alkaline metal salt. As the alkaline metal compound to be used there may be used the compound exemplified above. The amount of the alkaline metal compound to be used is from 1.2 to 2 mols per mol of phenol. For this As the halogen compound of the general formula (1m) to be used herein there may be used an oligomer or polymer wherein n is greater than 2 besides the monomer wherein n is 2. The oligomer or polymer can be obtained by allowing a bisphenol which is an etheric oxygen supply source as the electron-donating group B in the general formula (1m) and a combination of >C=O, —SO$_2$— and/or >C (CF$_3$)$_2$ as the electron-withdrawing group A, e.g., alkaline metal salt of bisphenol such as 2,2-bis(4-hydroxyphenyl)-1,1,1,3,3,3-hexafluoropropane, 2,2-bis(4-hydroxyphenyl)ketone and 2,2-bis(4-hydroxyphenyl)sulfone and activated aromatic halogen compound such as 4,4-dichlorobenzophenone and bis(4-chlorohenyl)sulfone in excessive amount to undergo substitution reaction in the presence of a polar solvent such as N-methyl-2-pyrrolidone, N,N-dimethylacetamide and sulfolane so that they are successively polymerized according to the foregoing method for synthesis of monomer. The oligomer or polymer may be subjected to ordinary purification for polymer such as dissolution-precipitation. For the adjustment of molecular weight of the product, the reaction molecular ratio of the excess aromatic dichloride and bisphenol may be used. Since the aromatic dichloride is present in excess, the resulting oligomer or polymer molecule is terminated by aromatic chloride. The resulting oligomer and polymer can be determined for number average molecular weight by GPC. The oligomer can be determined for number average molecular weight by NMR.

Specific examples of the structure of oligomer or polymer terminated by aromatic chloride will be given below.

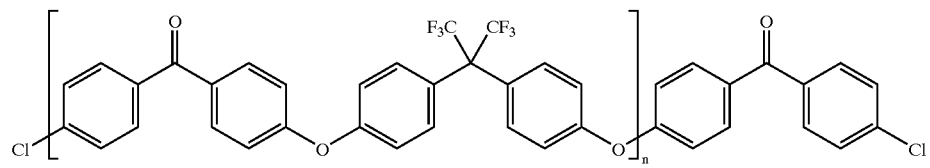

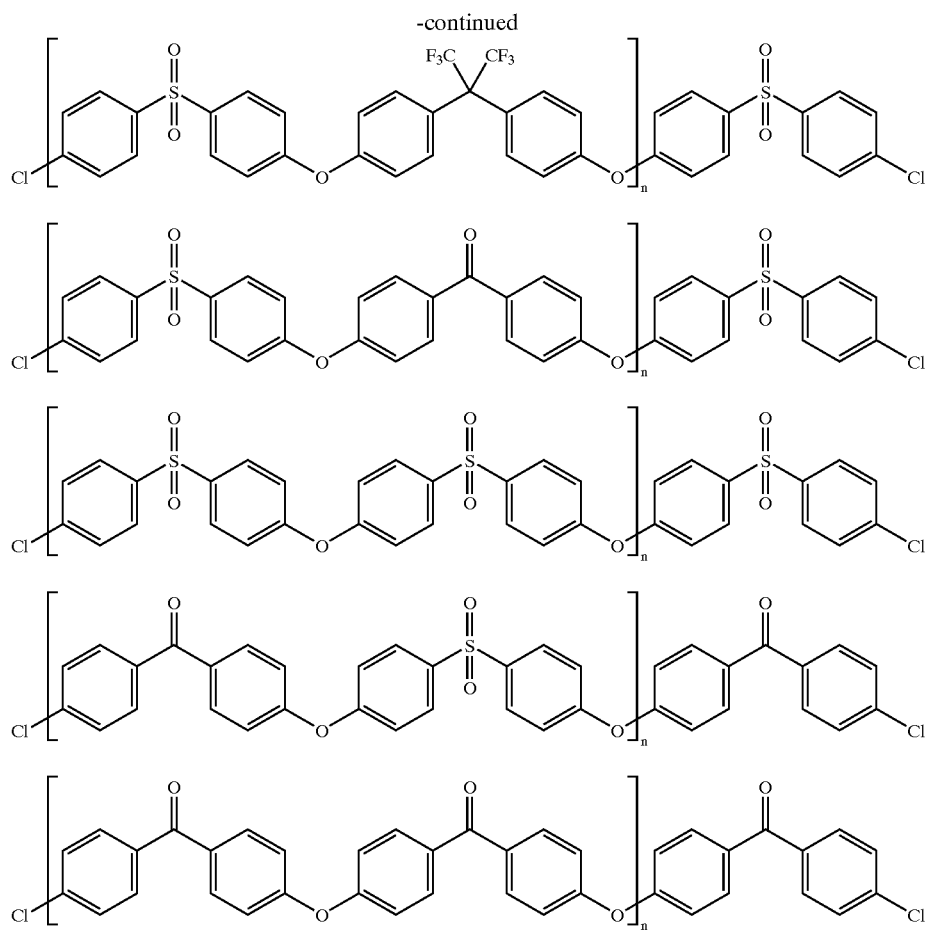

Polymer

The polymer of the invention may be a homopolymer comprising only the repeating unit represented by the general formula (1) (hereinafter referred to as "repeating unit (1)") or a copolymer comprising the repeating unit (1) and other repeating units. In either case, the polymer has a weight average molecular weight of from 10,000 to 1,000,000, preferably from 20,000 to 800,000 in polystyrene equivalence (hereinafter simply referred to as "weight average molecular weight") as measured by gel permeation chromatography.

In the case where the polymer has other repeating units, the content of the repeating unit (1) is preferably from 10 mol % to 80 mol %. When the content of the repeating unit (1) falls below 10 mol %, the resulting polymer cannot be expected to have an enhanced toughness.

The repeating unit (1) is formed by the monomer (1m) of the invention.

In the case where the polymer of the invention has repeating units other than the repeating unit (1) (hereinafter referred to as "other repeating units"), as the other repeating units there may be selected various units depending on the required properties and functions of polymer. In order to obtain a proton-conductive polymer, units represented by the general formulae (2) to (5) (hereinafter referred to as "unit (2), unit (3), unit (4) and unit (5)", respectively, or generically referred to as "unit (A)") may be used. The copolymer comprising the repeating unit (1) and the unit (A) can be sulfonated to produce a proton-conductive membrane material.

As the unit (A), the unit (2) is particularly desirable because its amount can be easily controlled when the polymer is sulfonated to incorporate a sulfonic acid group thereinto.

In the general formula (2) representing the unit (2), $R^9$ to $R^{15}$ each represent a hydrogen atom, fluorine atom or alkyl group. Examples of the alkyl group include methyl group, ethyl group, propyl group, butyl group, and hexyl group. The alkyl group may be fluorinated or may be a perfluoroalkyl group such as trifluoromethyl group and pentafluoroethyl group.

Examples of the aryl group represented by Z include phenyl group, naphthyl group, and biphenylyl group represented by the following general formula:

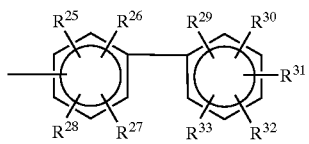

wherein $R^{25}$ to $R^{33}$ may be the same or different and each represent a hydrogen atom, fluorine atom or alkyl group. As the alkyl group there may be used one exemplified with reference to $R^9$ to $R^{15}$ in the general formula (1).

In the general formulae (3) to (5) representing the units (3) to (5), $R^{17}$ to $R^{24}$ each represent a hydrogen atom, alkyl group, fluorine atom, fluoroalkyl group or aryl group. Examples of the alkyl group include methyl group, ethyl group, propyl group, butyl group, and hexyl group.

Examples of the fluoroalkyl group include perfluoromethyl group, and perfluoroethyl group. Examples of the aryl group include phenyl group, tollyl group, and xylyl group.

The proportion of the repeating unit (A) in the polymer is preferably from 10 to 90 mol %, more preferably from 20 to 80 mol % of the copolymer. When the proportion of the repeating unit (A) is too small, the amount of sulfonic acid group to be incorporated into the copolymer by sulfonation tends to be insufficient, providing an insufficient proton conductivity.

The polymer of the invention can be obtained, e.g., by polymerizing or copolymerizing the monomer (1m) of the invention optionally with at least one monomer selected from the group consisting of the monomers corresponding to the other repeating units, e.g., monomers represented by the general formulae (2m) (3m), (4m) and (5m):

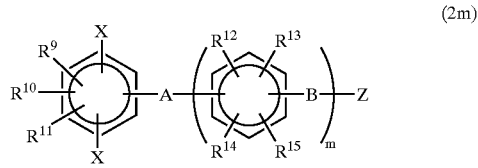

(2m)

wherein X, A and B are the same as defined in the general formula (1m); $R^9$ to $R^{15}$ may be the same or different and each represent a hydrogen atom, fluorine atom or alkyl group; and m and Z are the same as defined in the general formula (2);

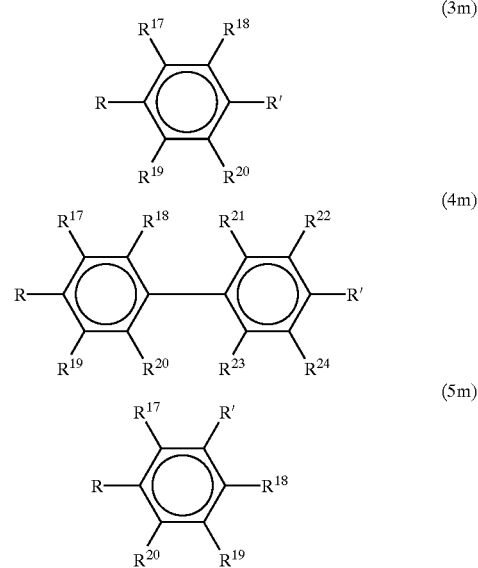

(3m)

(4m)

(5m)

wherein $R^{17}$ to $R^{24}$ are the same as defined in the general formulae (3) to (5); and R and R' each independently represent a halogen atom other than fluorine or group represented by the general formula $—OSO_2Y$ (in which Y represents an alkyl group, fluoroalkyl group or aryl group) corresponding to the repeating units (2), (3), (4) and (5), respectively, in the presence of a catalyst containing a transition metal compound.

In the general formulae (3m) to (5m), examples of the halogen represented by R and R', and the alkyl group, fluoroalkyl group and aryl group in Y include those exemplified with reference to $R^{17}$ to $R^{24}$ in the general formulae (3) to (5).

The sulfonic acid group-containing polymer of the invention can be obtained by sulfonating the polymer thus obtained as a precursor with a sulfonating agent.

Examples of the monomer (2m) include compounds represented by the following general formulae.

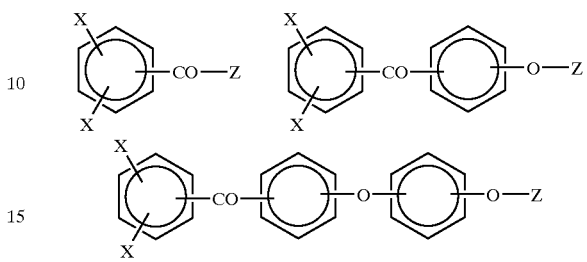

wherein X and Z are as defined in the general formula (2m).

Specific examples of the monomer (2m) include compounds represented by the following general formulae.

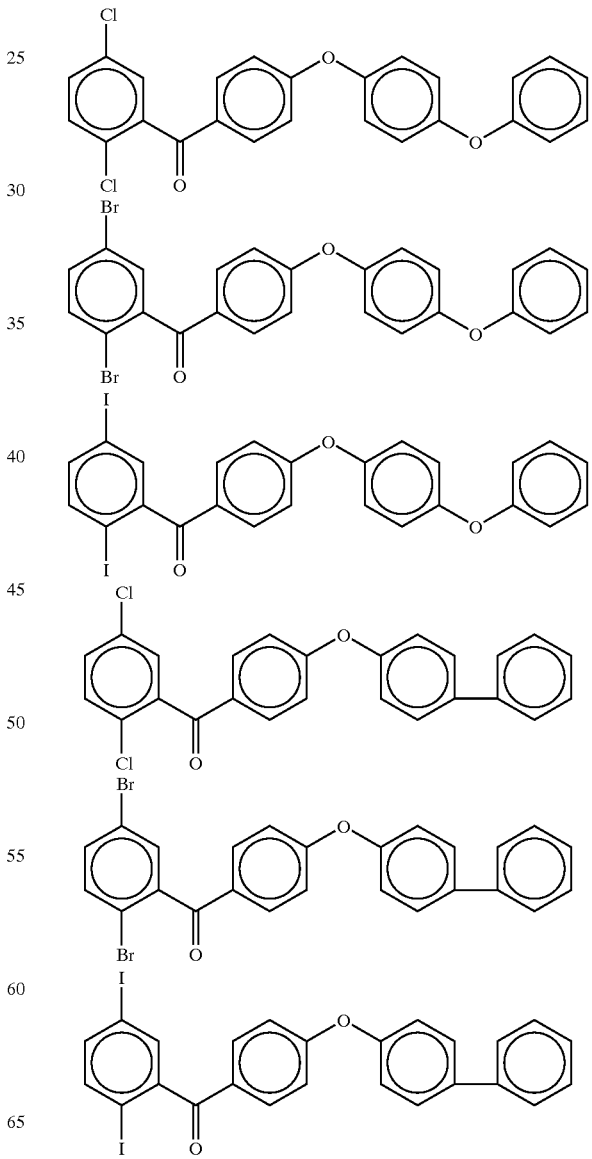

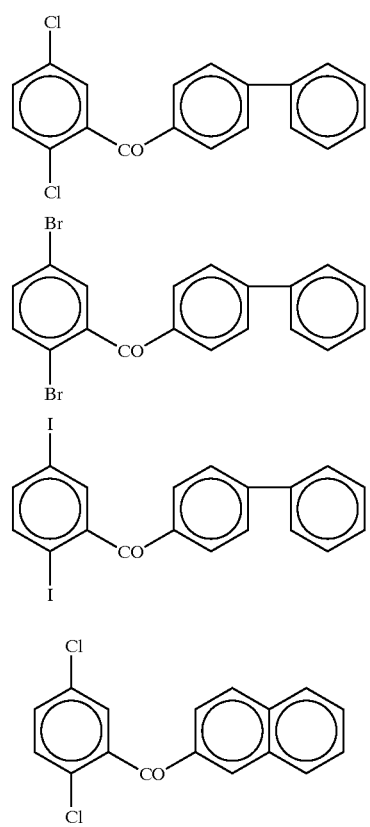

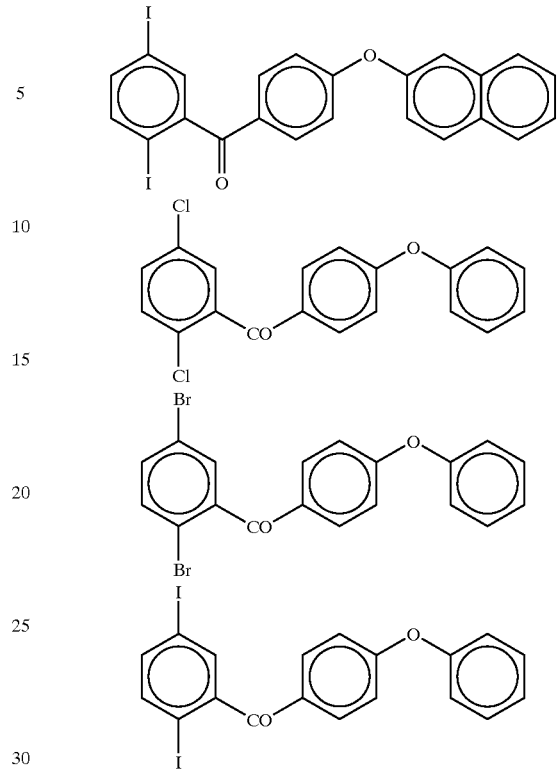

As the monomer (2m) there is preferably used a dichlorobenzoyl derivative such as 2,5-dichloro-4'-phenoxybenzophenone, 2,4-dichloro-4'-phenoxybenzophenone, 4'-phenoxyphenyl-2,5-dichlorobenzoate and 4'-phenoxyphenyl-2,4-dichlorobenzoate from the standpoint of solubility and polymerizability.

The monomer (2m), if it is 2,5-dichloro-4'-[4-(4-phenoxy)phenoxy]benzophenone by way of example, can be synthesized by the following reaction.

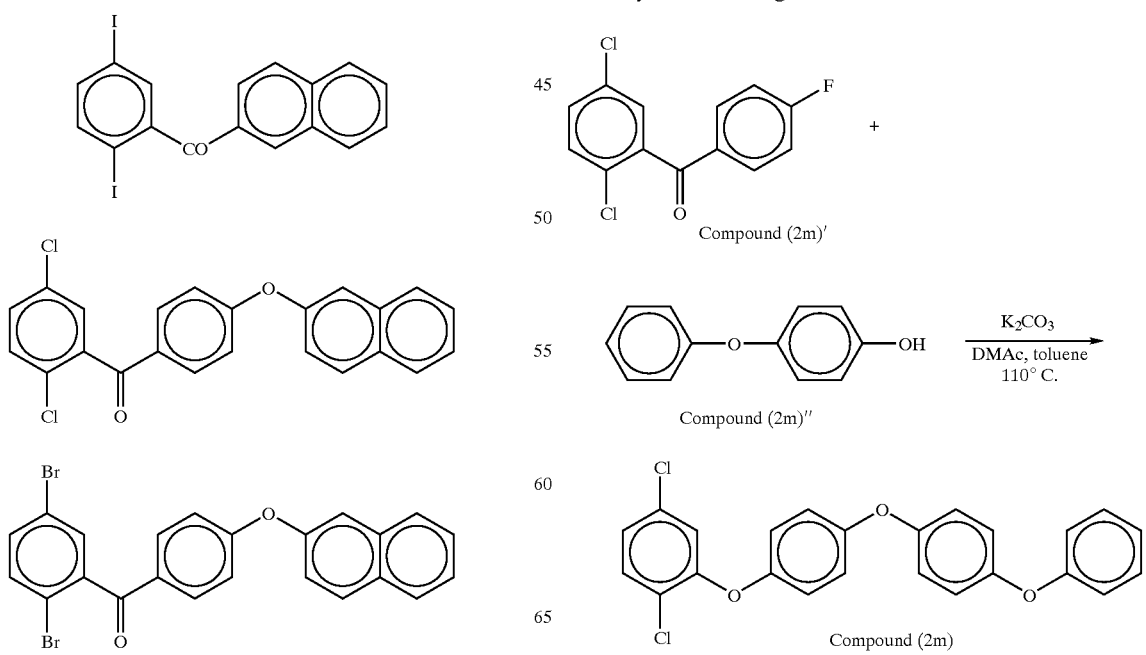

In some detail, the monomer (2m) can be synthesized by reacting a compound (2m)' (2,5-dichloro-4'-fluorobenzophenone) with a compound (2m)" (4-phenoxyphenol) in the presence of potassium carbonate or the like in a an aprotic dipole polar solvent such as dimethyl acetamide, N-methyl-2-pyrrolidone and dimethyl sulfoxide as a solvent and an azeotropic solvent for removing the resulting water from the reaction solution by azeotropy such as benzene, toluene and xylene at a temperature of from 80° C. to 200° C. for 0.5 to 30 hours. The compound (2m)" can be reacted normally in an amount almost equimolecular with the compound (2m)'.

The monomer (1) of the invention thus obtained can be identified for its structure by IR, NMR, elementary analysis, etc.

Specific examples of the monomer (3m) include p-dichlorobenzene, p-dibromobenzene, p-diodobenzene, p-dimethysulfonyloxybenzene, 2,5-dichlorotoluene, 2,5-dibromotoluene, 2,5-diodotoluene, 2,5-dimethylsulfonyloxybenzene, 2,5-dichloro-p-xylene, 2,5-dibromo-p-xylene, 2,5-diodo-p-xylene, 2,5-dichlorobenzotrifluoride, 2,5-dibromobenzotrifluoride, 2,5-diodobenzotrifluoride, 1,4-dichloro-2,3,5,6-tetrafluorobenzene, 1,4-dibromo-2,3,5,6-tetrafluorobenzene, and 1,4-diodo-2,3,5,6-tetrafluorobenzene. Preferred among these compounds are p-dibromobenzene, p-dimethysulfonyloxybenzene, and 2,5-dichlorobenzotrifluoride.

Specific examples of the monomer (4m) include 4,4'-dimethylsulfonyloxybiphenyl, 4,4'-dimethylsulfonyloxy-3,3'-dipropenylbiphenyl, 4,4'-dibromobiphenyl, 4,4'-diodobiphenyl, 4,4'-dimethylsulfonyloxy-3,3'-dimethylbiphenyl, 4,4'-dimethylsulfonyloxy-3,3'-difluorobiphenyl, 4,4'-dimethylsulfonyloxy-3,3',5,5'-tetraflurobiphenyl, 4,4'-dibromooctafluorobiphenyl, and 4,4'-dimethylsulfonyloxyoctafluorobiphenyl. Preferred among these compounds are 4,4'-dimethylsulfonyloxybiphenyl, 4,4'-dibromobiphenyl, 4,4'-diodobiphenyl, and 4,4'-dimethylsulfonyloxy-3,3'-dimethylbiphenyl.

Specific examples of the monomer (5m) include m-dichlorobenzene, m-dibromobenzene, m-diodobenzene, m-dimethylsulfonyloxybenzene, 2,4-dichlorotoluene, 2,4-dibromotoluene, 2,4-diodotoluene, 3,5-dichlorotoluene, 3,5-dibromotoluene, 3,5-diodotoluene, 2,6-dichlorotoluene, 2,6-dibromotoluene, 2,6-diodotoluene, 3,5-dimethylsulfonyloxytoluene, 2,6-dimethylsulfonyloxytoluene, 2,4-dichlorobenzotrifluoride, 2,4-dibromobenzotrifluoride, 2,4-diodobenzotrifluoride, 3,5-dichlorobenzotrifluoride, 3,5-dibromotrifluoride, 3,5-diodobenzotrifluoride, and 1,3-dibromo-2,4,5,6-tetrafluorobenzene. Preferred among these compounds are m-dichlorobenzene, 2,4-dichlorotoluene, 3,5-dimethylsulfonyloxytoluene, and 2,4-dichlorobenzotrifluoride.

In the case where the copolymer comprising the repeating unit (1) and the repeating unit (A) is synthesized, the proportion of the monomer (1) represented by the general formula (1m) and at least one monomer (A) selected from the group consisting of compounds represented by the general formulae (2m) to (5m) is the same as the proportion of the unit (1) and the unit (A) in the polymer. In other words, the amount of the monomer (1) to be used is preferably from 3 to 40 mol %, more preferably from 5 to 35 mol % based on the total amount of the monomers. The amount of the monomer (A) to be used is preferably from 60 to 97 mol %, more preferably from 65 to 95 mol % based on the total amount of the monomers.

In particular, the proportion of the monomer (2m) to be used as the monomer (A) is preferably not smaller than 10 mol %, more preferably not smaller than 20 mol % based on the total amount of the monomers. When the proportion of the monomer (2m) falls within the above defined range, a good solubility and a high molecular compound can be obtained.

In particular, the proportion of the monomer (3m) to be used is preferably not smaller than 10 mol %, more preferably not smaller than 20 mol % based on the total amount of the monomers. When the proportion of the monomer (3m) falls within the above defined range, a good solubility and a high molecular compound can be obtained.

In particular, the proportion of the monomer (4m) to be used is preferably not smaller than 50 mol %, more preferably not smaller than 30 mol % based on the total amount of the monomers. When the proportion of the monomer (4m) falls within the above defined range, a good solubility and a high molecular compound can be obtained.

The proportion of the monomer (5m) to be used is preferably not greater than 50 mol %, more preferably not greater than 30 mol % based on the total amount of the monomers.

The catalyst to be used in the production of the copolymer of the invention is a catalyst containing a transition metal compound. This catalyst system comprises as essential components (i) a transition metal salt and a compound as ligand (hereinafter referred to as "ligand component") or a transition metal complex (including copper salt) having ligands oriented therein and (ii) a reducing agent. In order to raise the polymerization speed, the catalyst system may comprise a "salt" incorporated therein.

Examples of the transition metal salt employable herein include nickel compounds such as nickel chloride, nickel bromide, nickel iodide and nickel acetylatonate, palladium compounds such as palladium chloride, palladium bromide and palladium iodide, iron compounds such as iron chloride, iron bromide and iron iodide, and cobalt compounds such as cobalt chloride, cobalt bromide and cobalt iodide. Particularly preferred among these transition metal salts are nickel chloride and nickel bromide.

Examples of the ligand component employable herein include triphenyl phosphine, 2,2'-bipyridine, 1,5-cyclooctadiene, and 1,3-bis(diphenylphosphino)propane. Preferred among these ligand components are triphenyl phosphine and 2,2'-bipyridine. These compounds as ligand components may be used singly or in combination of two or more thereof.

Examples of the transition metal complex having ligands oriented therein employable herein include nickel chloride bis(triphenylphosphine), nickel bromide bis(triphenylphosphine), nickel iodide bis(triphenylphosphine), nickel nitrate bis(triphenylphosphine), nickel chloride(2,2'-bipyridine), nickel bromide(2,2'-bipyridine), nickel iodide (2,2'-bipyridine), nickel nitrate(2,2'-bipyridine), bis(1,5-cycloctadiene)nickel, tetrakis(triphenylphosphine)nickel, tetrakis(triphenylphosphite)nickel, and tetrakis (triphenylphosphine)palladium. Preferred among these transition metal complexes are nickel chloride bis(triphenylphosphine), and nickel chloride(2,2'-bipyridine).

Examples of the reducing agent which can be incorporated in the catalyst system include iron, zinc, manganese, aluminum, magnesium, sodium, and calcium. Preferred among these reducing agents are zinc, magnesium, and manganese. These reducing agents may be allowed to come in contact with an acid such as organic acid so that it is further activated.

Examples of the salt which can be incorporated in the catalyst system include sodium compounds such as sodium fluoride, sodium chloride, sodium bromide, sodium iodide and sodium sulfate, potassium compounds such as potassium fluoride, potassium chloride, potassium bromide, potassium iodide and potassium sulfate, and ammonium compounds such as tetraethylammonium fluoride, tetraethylammonium chloride, tetraethylammonium bromide, tetraethylammonium iodide and tetraethylammonium sulfate. Preferred among these salts are sodium bromide, sodium iodide, potassium bromide, tetraethylammonium bromide, and tetraethylammonium iodide.

The proportion of the transition metal salt or transition metal complex in the catalyst system is normally from 0.0001 to 10 mols, preferably from 0.01 to 0.5 mols per mol of the total amount of the monomers. When the proportion of the transition metal salt falls below 0.0001 mols, the polymerization reaction cannot proceed sufficiently. On the contrary, when the proportion of the transition metal salt exceeds 10 mols, the resulting catalyst system has a reduced molecular weight.

In the case where the catalyst system comprises a transition metal salt and a ligand component incorporated therein, the proportion of the ligand component is normally from 0.1 to 100 mols, preferably from 1 to 10 mols per mol of the transition metal salt. When the proportion of the ligand component falls below 0.1 mols, the resulting catalytic activity is insufficient. On the contrary, when the proportion of the ligand component exceeds 100 mols, the resulting catalyst system has a reduced molecular weight.

The proportion of the reducing agent in the catalyst system is normally from 0.1 to 100 mols, preferably from 1 to 10 mols per mol of the total amount of the monomers. When the proportion of the reducing agent falls below 0.1 mols, the polymerization reaction cannot proceed sufficiently. On the contrary, when the proportion of the reducing agent exceeds 100 mols, the resulting polymer can difficultly be purified.

In the case where the catalyst system comprises a "salt" incorporated therein, the amount of the salt to be used is normally from 0.001 to 100 mols, preferably from 0.01 to 1 mol per mol of the total amount of the monomers. When the amount of the salt to be used falls below 0.001 mols, the effect of raising the polymerization speed is insufficient. On the contrary, when the amount of the salt to be used exceeds 100 mols, the resulting polymer can difficultly be purified.

Examples of the polymerizing solvent employable herein include tetrahydrofurane, cyclohexanone, dimethyl sulfoxide, N,N-dimethylformamide, N,N-dimethylacetamide, N-methyl-2-pyrrolidone, γ-butyrolactone, and γ-butyrolactam. Preferred among these solvents for polymerization are tetrahydrofurane, N,N-dimethylformamide, N,N-dimethylacetamide, and N-methyl-2-pyrrolidone. These polymerizing solvents are preferably thoroughly dried before use.

The total concentration of the monomers in the solvent for polymerization is normally from 1 to 90% by weight, preferably from 5 to 40% by weight.

The polymerization temperature at which the copolymer of the invention is produced is normally from 0° C. to 200° C., preferably from 50° C. to 120° C. The polymerization time is normally from 0.5 to 100 hours, preferably from 1 to 40 hours.

The monomer (1m) and the monomer (2m), for example, can be subjected to polymerization under the foregoing conditions to obtain a copolymer represented by the following general formula:

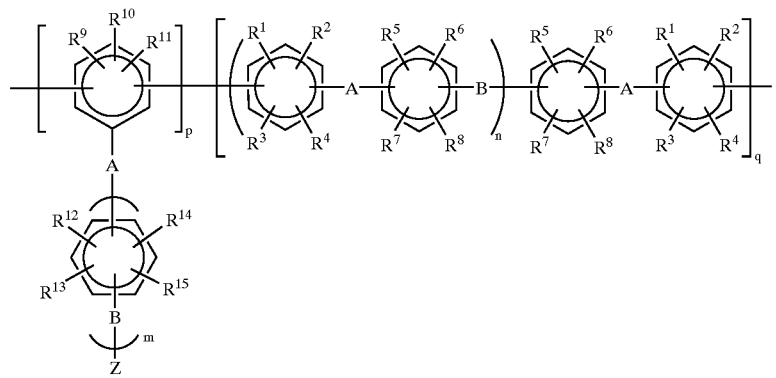

wherein A, B, Z, $R^1$ to $R^{15}$, m and n are the same as defined above; and p and q each independently represent the number of the respective repeating units, with the proviso that the ratio p/q (i.e., the molar ratio of the two repeating units) is from 99/1 to 20/80.

The structure of the copolymer of the invention can be confirmed by C—O—C absorption at a wavelength of from 1,230 to 1,250 $cm^{-1}$, C=O absorption at a wavelength of from 1,640 to 1,660 $cm^{-1}$, or the like on infrared absorption spectrum. The structure of the copolymer of the invention can be confirmed also by the peak of aromatic proton of from 6.8 to 8.0 ppm on nuclear magnetic resonance spectrum ($^1$H-NMR).

The copolymer having a sulfonic acid group to be used for the conductive membrane of the invention can be obtained by introducing a sulfonic acid group into the foregoing copolymer free of sulfonic acid group using a sulfonating agent according to an ordinary method.

In order to incorporate a sulfonic acid group into the copolymer free of sulfonic acid group, the copolymer free of sulfonic acid group can be subjected to sulfonation using a known sulfonating agent such as sulfuric anhydride, fuming sulfuric acid, chlorosulfonic acid, sulfuric acid and sodium hydrogensulfite under known conditions [Polymer Preprints, Japan, Vol. 42, No. 3, p. 730 (1993); Polymer Preprints, Japan, Vol. 43, No. 3, p. 736 (1994); Polymer Preprints, Japan, Vol. 42, No. 7, p. 2490–2492 (1993)].

Referring further to the sulfonation conditions, the copolymer free of sulfonic acid group is reacted with the sulfonating agent in the absence or presence of solvent. Examples of the solvent employable herein include hydrocarbon solvent such as n-hexane, ether-based solvent such as tetrahydrofurane and dioxane, aprotic polar solvent such as dimethylacetamide, dimethylformamide and dimethyl sulfoxide, and halogenated hydrocarbon such as tetrachloroethane, dichloroethane, chloroform and methylene chloride. The reaction temperature is not specifically limited but is normally from −50° C. to 200° C., preferably from −10° C. to 100° C. The reaction time is normally from 0.5 to 1,000 hours, preferably from 1 to 200 hours.

The amount of the sulfonic acid group in the sulfonic acid group-containing copolymer of the invention thus obtained is from 0.5 to 3 mg equivalent/g, preferably from 0.8 to 2.8 mg equivalent/g. When the amount of the sulfonic acid group falls below 0.5 mg equivalent/g, the resulting copolymer does not exhibit an increased proton conductivity. On the contrary, when the amount of the sulfonic acid group exceeds 3 mg equivalent/g, the resulting copolymer has a raised hydrophilicity to an extent such that it becomes a water-soluble polymer or has a deteriorated durability, though not going so far as being water-soluble.

The amount of the sulfonic acid group can be easily adjusted by changing the proportion of the monomer (1) and the monomer (A), the kind and combination of the monomer (A).

The molecular weight of the unsulfonated precursor of the sulfonic acid group-containing copolymer of the invention thus obtained is from 10,000 to 1,000,000, preferably from 20,000 to 800,000 as calculated in terms of weight-average molecular weight in polystyrene equivalence. When the molecular weight of the unsulfonated precursor falls below 10,000, the resulting unsulfonated precursor exhibits so insufficient coatability that the film thus formed undergoes cracking and exhibits an insufficient strength. On the contrary, when the molecular weight of the unsulfonated precursor exceeds 1,000,000, the resulting unsulfonated precursor exhibits an insufficient solubility and a high solution viscosity and hence a poor workability.

The structure of the sulfonic acid group-containing copolymer of the invention can be confirmed by S=O absorption at a wavelength of from 1,030 to 1,045 $cm^{-1}$ and from 1,160 to 1,190 $cm^{-1}$, C—O—C absorption at a wavelength of from 1,130 to 1,250 $cm^{-1}$ and C=O absorption at a wavelength of from 1,640 to 1,660 $cm^{-1}$ on infrared absorption spectrum. The composition ratio of these components can be determined by neutralization titration of sulfonic acid or elementary analysis. The structure of the copolymer of the invention can be confirmed also by the peak of aromatic proton of from 6.8 to 8.0 ppm on nuclear magnetic resonance spectrum ($^1$H-NMR).

The conductive membrane of the invention is made of the sulfonic acid group-containing copolymer. However, the conductive membrane may further comprises an inorganic acid such as sulfuric acid and phosphoric acid, an organic acid such as carboxylic acid, a proper amount of water, etc. incorporated therein besides the sulfonic acid group-containing copolymer.

In order to produce the conductive membrane of the invention, the sulfonic acid group-containing copolymer of the invention may be dissolved in a solvent, and then subjected to casting method involving casting for making film or melt forming method.

Examples of the solvent to be used in the casting method include aprotic polar solvents such as dimethylacetamide, dimethylformamide, N-methyl-2-pyrrolidone and dimethyl sulfoxide. These solvents may be mixed with an alcohol solvent such as methanol.

The conductive membrane of the invention can be used as a proton-conductive membrane for primary battery electrolyte, secondary battery electrolyte, fuel cell polymer solid electrolyte, display element, various sensors, signal transfer medium, solid capacitor, ion exchange membrane, etc.

The invention will be further described in the following examples, but the invention should not be construed as being limited thereto.

The various properties to be measured in the examples were determined in the following manner.

Weight-average molecular weight

For the determination of the weight-average molecular weight of the unsulfonated precursor polymer, the molecular weight in polystyrene equivalence was measured with tetrahydrofurane as a solvent by gel permeation chromatography (GPC).

Amount of sulfonic acid group

The sulfonated polymer thus obtained was washed with water until the wash water exhibited a pH value of from 4 to 6 so that remaining free acid was removed. The sulfonated polymer was thoroughly washed with water, dried, and then measured out in a predetermined amount. The sulfonated polymer was dissolved in a mixture of THF and water. The solution was then neutralized with a standard NaOH solution with phenolphthalein as an indicator. From the neutralization point, the amount of sulfonic acid group (mg equivalent/g) was determined.

Tensile strength

A test specimen was prepared by forming a 50 $\mu$m thick film of sulfonated polymer having a size of 3 mm wide×65 mm long (distance between chucks: 25 mm). Using a tensile testing machine, the test specimen was measured for elastic modulus, breaking strength, yield strength and elongation at room temperature.

Flexing resistance

Using a flexing resistance testing machine, a 50 $\mu$m thick sulfonated polymer film was bent at a rate of 166 times/min, a load of 200 g and a flex deformation angle of 1350. Those which can be bent 500 or more times until they break are considered good. Those which can be bent less than 500 times are considered poor.

Measurement of proton conductivity

For the measurement of a.c. resistivity, the a.c. impedance across platinum wires (diameter: 0.5 mm) pressed against the surface of a 5 mm wide strip-shaped film specimen kept in a constant temperature and humidity device was determined. In some detail, the impedance was measured at 10 KHz at a temperature of 85° C. and a relative humidity of 90%.

As the resisitivity meter there was used a chemical impedance measurement system produced by NF Corporation. As the constant temperature and humidity device there was used JW241, produced by Yamato Chemical Co., Ltd. Five platinum wires were pressed against the surface of the test specimen at an interval of 5 mm. With the distance between the electrodes varied from 5 mm to 20 mm, the a.c. resistivity was measured.

The distance between the electrodes and the resistivity gradient were then substituted in the following equation to calculate the specific resistivity of the film. The reciprocal of the specific resistivity was then calculated to determine the a.c. impedance.

Specific resistivity [Ω·cm]=0.5 [cm]×film thickness [cm]× resistivity gradient between electrodes [Ω/cm]

Thermal properties

Thermal decomposition temperature:

The decomposition temperature of the sulfonated polymer measured by TGA (at a temperature rising rate of 20° C./min in a nitrogen atmosphere) was defined as thermal decomposition temperature.

Glass transition temperature:

The temperature at which the test specimen shows a heat capacity change by DSC (at a temperature rising rate of 20° C./min in a nitrogen atmosphere) was defined as glass transition temperature.

Hot water resistance:

A 50 μm thick sulfonated polymer film was dipped in a 95° C. water for 5 hours. Those showing a dimensional change of less than 50% are considered good. Those showing a dimensional change of not smaller than 50% and melting are considered poor.

EXAMPLE 1

Synthesis of 2,2-bis[4-{4-(4-chlorobenzoyl)phenoxy}phenyl]-1,1,1,3,3,3-hexafluoropropane (BCPAF)

33.6 g (100 mmol) of 2,2-bis(4-hydroxyphenyl)-1,1,1,3,3,3-hexafluoropropane (bisphenol AF) was measured out in a 1 l three-necked flask equipped with an agitator, a Dean-stark tube, a condenser, a three-way cock and a thermometer. The air in the flask was then replaced by dried nitrogen. To the content of the flask were then added 150 ml of N,N-dimethylacetamide and 75 ml of toluene. The mixture was then stirred for dissolution. To the solution was then added 30.4 g (220 mmol) of potassium carbonate. The mixture was then heated to a temperature of 130° C. under reflux. While the resulting water was being boiled together with toluene and removed to the exterior through the Dean-Stark trap, the reaction temperature was then gradually raised to 150° C. After about 1 hour, when most of toluene was removed, the reaction solution was then cooled to a temperature of from 80° C. to 90° C. Subsequently, to the reaction solution was added 58.7 g (250 mmol) of 4-chloro-4'-fluorobenzophenone. The reaction solution was then reacted at a temperature of from 115° C. to 120° C. for 7 hours.

After the reaction solution was allowed to cool, the inorganic materials were then removed by filtration. The filtrate was then poured into 500 ml of methanol. The resulting precipitate was withdrawn by filtration, washed with methanol, and then dried. 75 g of the resulting crude product was then recrystallized from 165 ml of toluene to obtain 65 g (85%) of the desired product (melting point: 168° C. to 170° C.)

Figure 2:
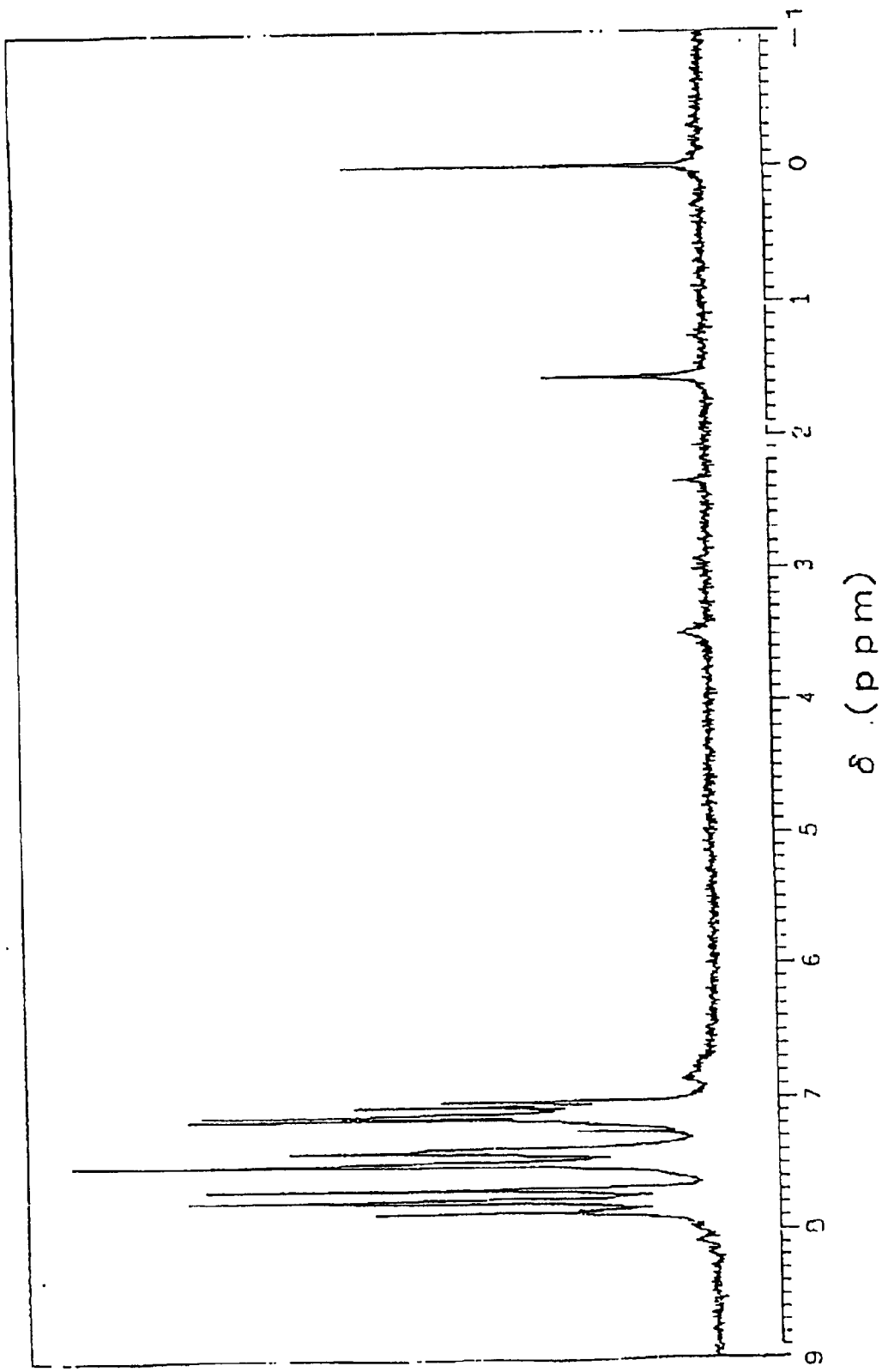
FIG. 2 is a diagram illustrating NMR spectrum of the compound of FIG. 1.

The infrared absorption spectrum of the product is shown in FIG. 1. The NMR spectrum of the product is shown in FIG. 2.

EXAMPLE 2

Figure 3:
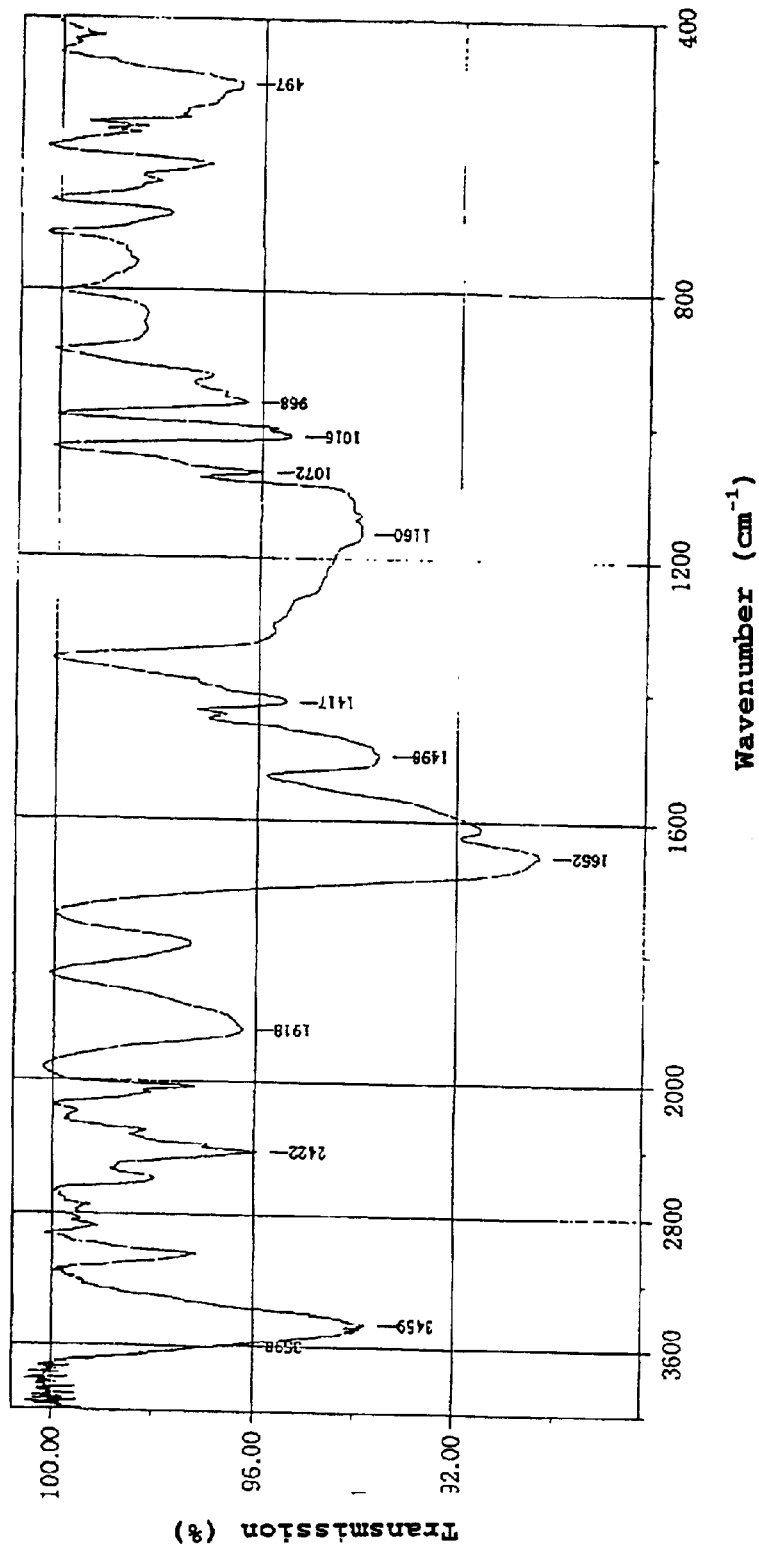
FIG. 3 is an IR spectrum of the copolymer obtained in Example 2.

(1) Preparation of 50:50 copolymer of 2,5-dichloro-4'-(4-phenoxy)phenoxybenzophenone and 2,2'-bis[4-(4-chlorobenzoyl)phenoxy]diphenyl-1,1,1,3,3,3-hexafluoropropane 22.8 g (35 mmol) of 2,5-dichloro-4'-(4-phenoxy)phenoxybenzophenone, 26.7 g (35 mmol) of 2,2'-bis[4-(4-chlorobenzoyl)phenoxy]diphenyl-1,1,1,3,3,3-hexafluoropropane, 1.57 g (2.4 mmol) of bis(triphenylphosphine)nickel dichloride, 1.56 g (10.4 mmol) of sodium iodide, 8.39 g (32 mmol) of triphenylphosphine and 12.6 g (192 mmol) of zinc were measured out in a flask. The air in the flask was then replaced by dried nitrogen. To the content of the flask was then added 100 ml of N-methyl-2-pyrrolidone (NMP). The mixture was heated to a temperature of 70° C. where it was then stirred for polymerization reaction for 3 hours. The reaction solution was then poured into 3,000 ml of a 9:1 (by volume) mixture of methanol and concentrated hydrochloric acid. The resulting product was then solidified and precipitated. The resulting precipitate was withdrawn by filtration, washed with methanol, and then dried in vacuo to obtain 35 g (95%) of the desired copolymer. The IR spectrum of the copolymer thus obtained is shown in FIG. 3. The number-average molecular weight and weight-average molecular weight of the copolymer determined by GPC were 29,400 and 60,500, respectively. The copolymer exhibited a glass transition temperature of 168° C. and a thermal decomposition starting temperature of 336° C. in a nitrogen atmosphere. The film prepared from the copolymer exhibited an elastic modulus of 2.6 GPa, a yield stress of 95 MPa, a yield elongation of 6%, a tensile strength of 87 MPa and an elongation at break of 10%, demonstrating that it is ductile.

Figure 4:
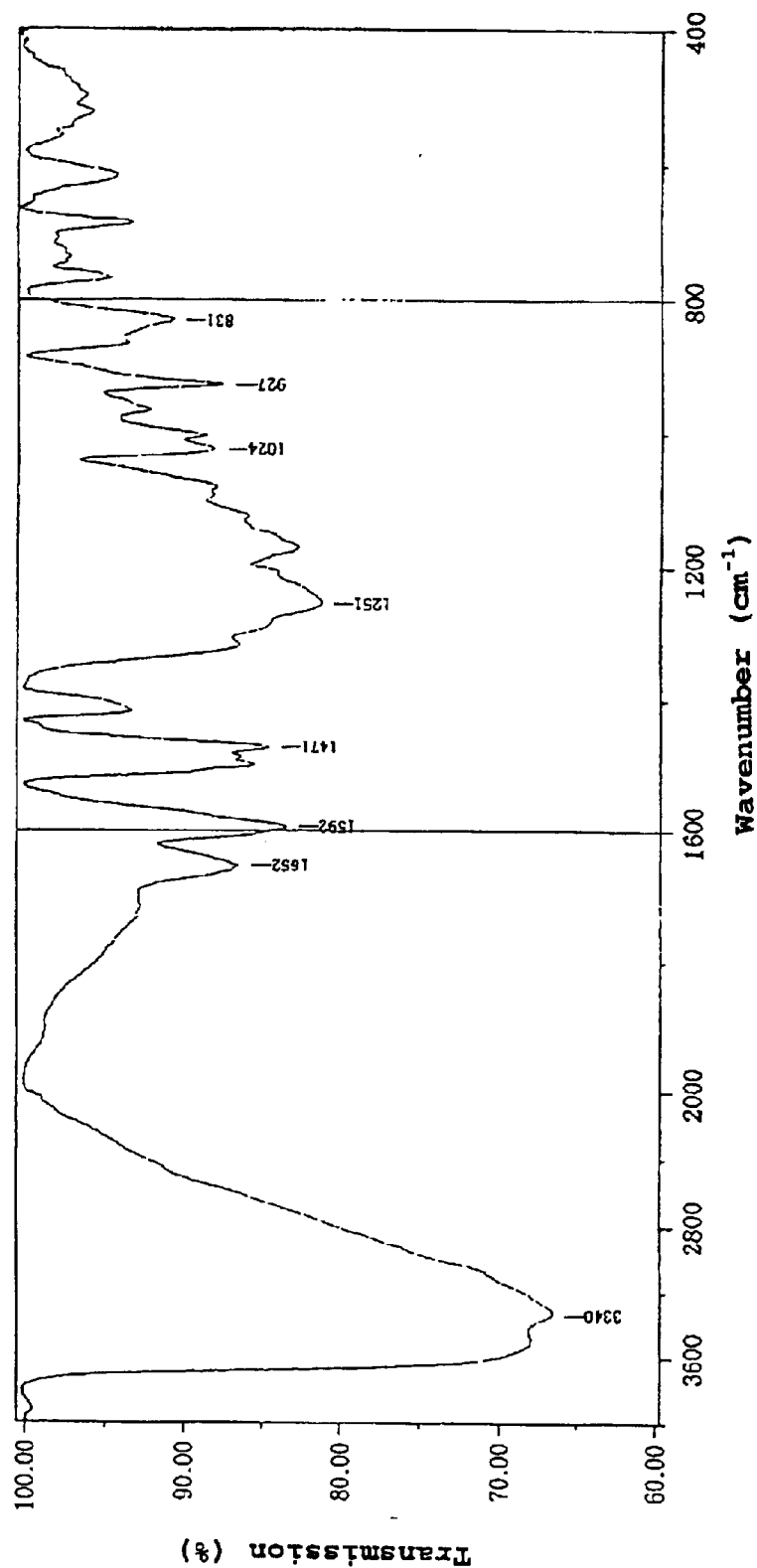
FIG. 4 is an IR spectrum of the sulfonated copolymer obtained in Example 2.

(2) Preparation of 50:50 Copolymer of 2,5-dichloro-4'-(4-phenoxy)phenoxybenzophenone and 2,2'-bis[4-(4-chlorobenzoyl)phenoxy]diphenyl-1,1,1,3,3,3-hexafluoropropane To 20 g of the copolymer thus obtained was added 200 ml of concentrated sulfuric acid. The mixture was then stirred at a temperature of 60° C. for 5 hours. The reaction solution was then poured into water so that the polymer was precipitated. The polymer was repeatedly washed with water until the pH value of the wash water reached 5. The polymer was then dried to obtain 25 g (95%) of a sulfonated polymer. The infrared absorption spectrum of the sulfonated polymer is shown in FIG. 4.

The characteristics of the sulfonated polymer thus obtained are set forth in Table 1.

EXAMPLE 3

Figure 5:
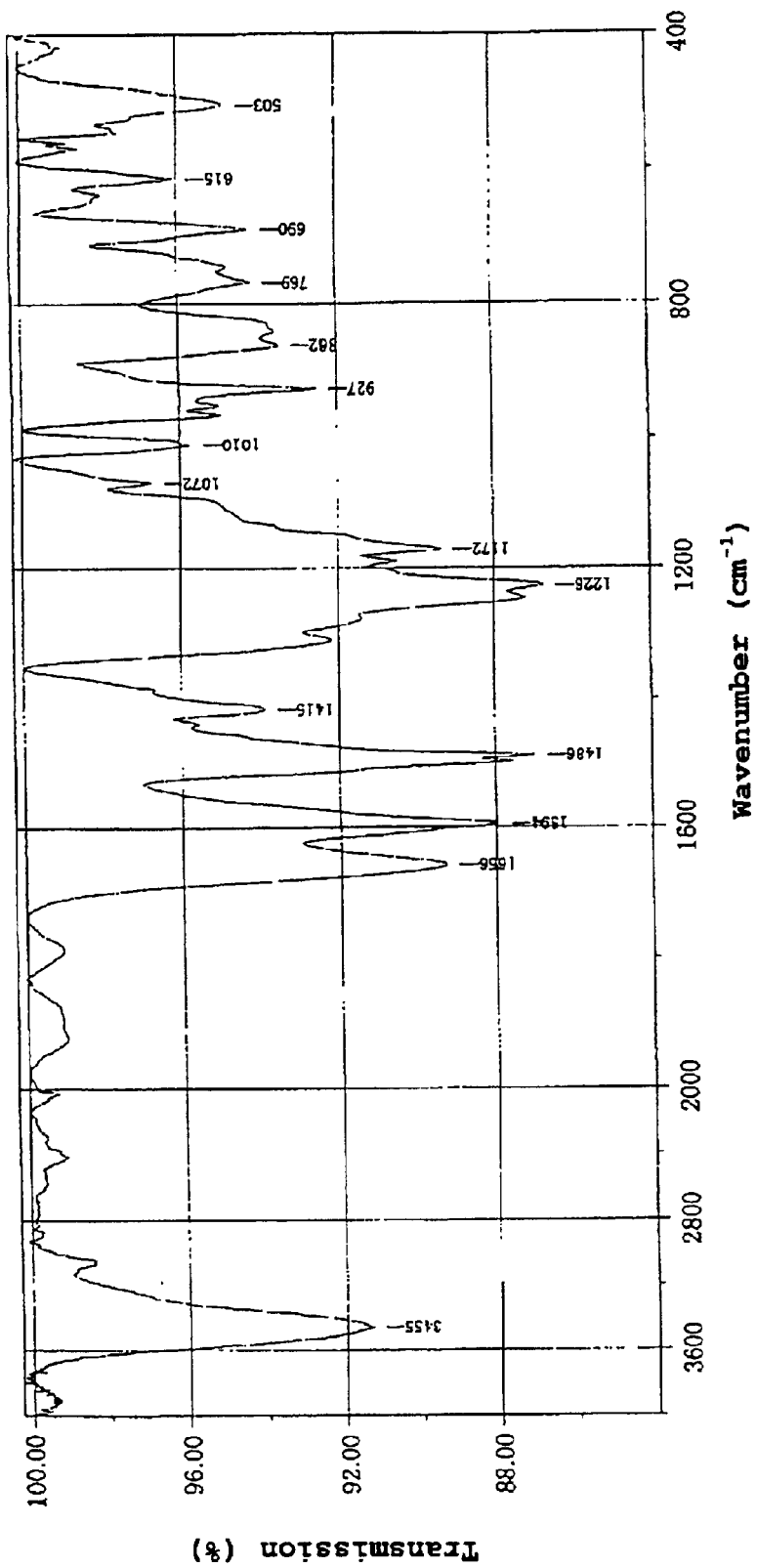
FIG. 5 is an IR spectrum of the copolymer obtained in Example 3.

(1) Preparation of 70:30 copolymer of 2,5-dichloro-4'-(4-phenoxy)phenoxybenzophenone and 2,2'-bis[4-(4-chlorobenzoyl)phenoxy]diphenyl-1,1,1,3,3,3-hexafluoropropane The polymerization procedure of Example 1 was followed except that 24.4 g (56 mmol) of 2,5-dichloro-4'-(4-phenoxy)phenoxybenzophenone and 18.3 g (24 mmol) of 2,2'-bis[4-(4-chlorobenzoyl)phenoxy]diphenyl-1,1,1,3,3,3-h exafluoropropane were used. As a result, 35 g (95%) of a copolymer was obtained. The number-average molecular weight and weight-average molecular weight of the polymer determined by GPC were 27,800 and 60,200, respectively. The IR spectrum of the copolymer thus obtained is shown in FIG. 5. The copolymer exhibited a glass transition temperature of 155° C. and a thermal decomposition starting temperature of 384° C. in a nitrogen atmosphere.

Figure 6:
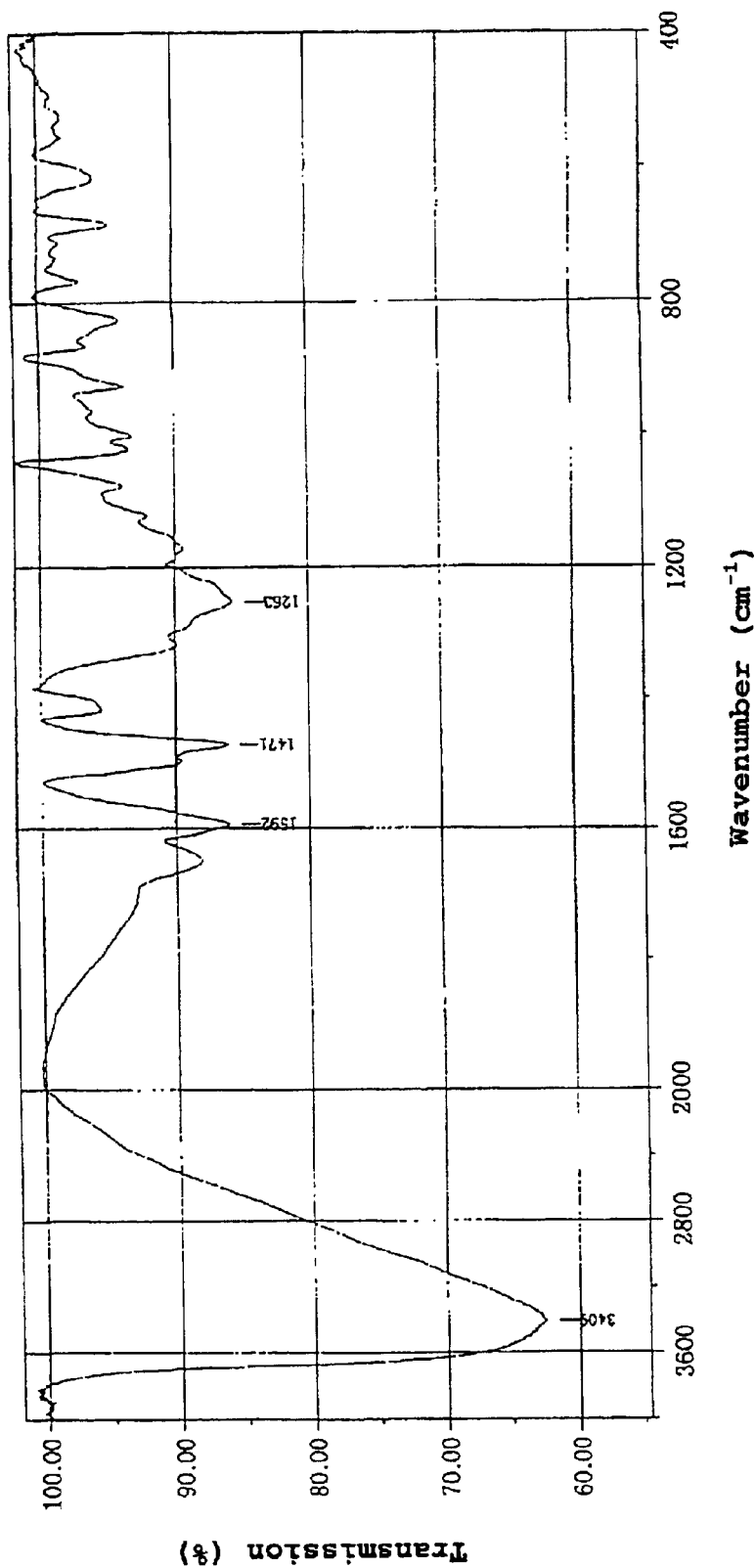
FIG. 6 is an IR spectrum of the sulfonated copolymer obtained in Example 3.

(2) Preparation of sulfonation product of 70:30 copolymer of 2,5-dichloro-4'-(4-phenoxy)phenoxybenzophenone and 2,2'-bis[4-(4-chlorobenzoyl)phenoxy]diphenyl-1,1,1,3,3,3-hexafluoropropane To 20 g of the copolymer thus obtained was then added 200 ml of concentrated sulfuric acid. The mixture was then stirred at a temperature of 60° C. for 5 hours. The reaction solution was then poured into water so that the polymer was precipitated. The polymer was repeatedly washed with water until the pH value of the wash water reached 5. The polymer was then dried to obtain 23 g (93%) of a sulfonated polymer. The infrared absorption spectrum of the sulfonated polymer is shown in FIG. 6.

The characteristics of the sulfonated polymer thus obtained are set forth in Table 1.

COMPARATIVE EXAMPLE 1

(1) Preparation of homopolymer of 2,5-dichloro-4'-phenoxybenzophenone

The polymerization procedure and subsequent treatment procedure of Example 1 were followed except that only 24.0 g (70 mmol) of 2,5-dichloro-4'-phenoxybenzophenone was used instead of 22.8 g (35 mmol) of 2,5-dichloro-4'-(4-phenoxy)phenoxybenzophenone and 26.7 g (35 mmol) of 2,2'-bis[4-(4-chlorobenzoyl)phenoxy]diphenyl-1,1,1,3,3,3-hexafluoropropane.

Mn and Mw of the polymer determined by GPC were 34,800 and 95,100, respectively. The polymer exhibited a glass transition temperature of 152° C. and a 5% thermal decomposition temperature of 404° C. in a nitrogen atmosphere. The film prepared from the copolymer an elastic modulus of 2.2 GPa, a tensile strength of 2.1 MPa and an elongation at break of 3% and thus underwent breakage when bent.

(2) Preparation of sulfonation product of homopolymer of 2,5-dichloro-4'-phenoxybenzophenone To 20 g of the homopolymer thus obtained was then added 200 ml of concentrated sulfuric acid. The mixture was then stirred at room temperature for 5 hours. The reaction solution was then poured into water so that the polymer was precipitated. The polymer was then repeatedly washed with water until the pH value of the wash water reached 5. The polymer was then dried to obtain 23 g (93%) of a sulfonated polymer.

The characteristics of the sulfonated polymer thus obtained are set forth in Table 1.

product was then recrystallized from 160 ml of toluene to obtain 58 g (85%) of the desired product (melting point: 191° C. to 195° C.).

Figure 7:
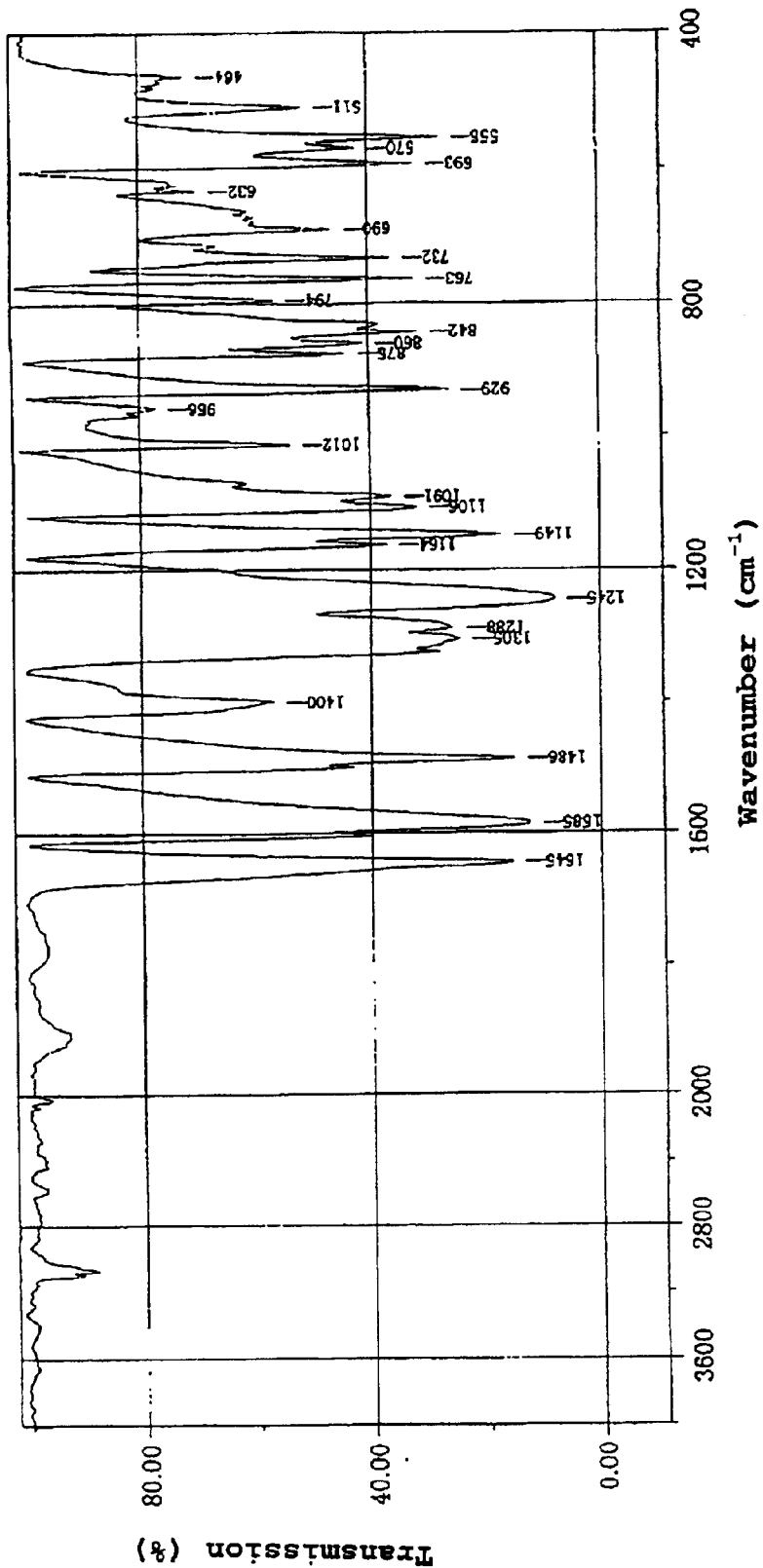
FIG. 7 is an IR spectrum of 4,4'-bis[(4-chlorobenzoyl)phenoxy]diphenylsulfone (BCPES) as a halogenated aromatic compound of the invention obtained in Example 4.
Figure 8:
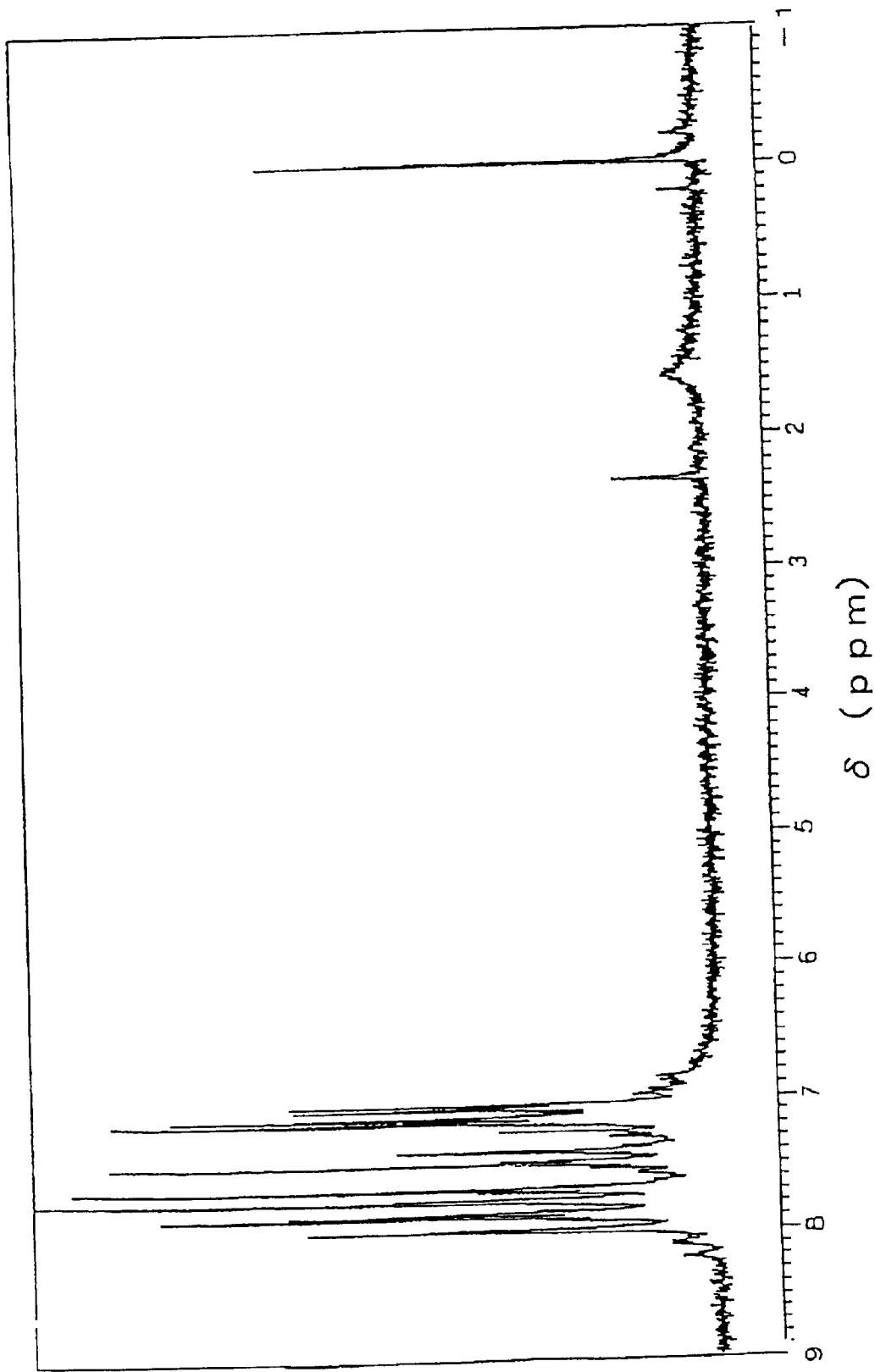
FIG. 8 is a diagram illustrating NMR spectrum of the compound of FIG. 7.

The infrared absorption spectrum of the product is shown in FIG. 7. The NMR spectrum of the product is shown in FIG. 8.

EXAMPLE 5

(1) Preparation of 60:40 copolymer of 2,5-dichloro-4'-(4-phenoxy)phenoxybenzophenone and 4,4'-bis[(4-chlorobenzoyl)-phenoxy]diphenylsulfone 24.4 g (48 mmol) of 2,5-dichloro-4'-(4-phenoxy) phenoxybenzophenone, 16.3 g (32 mmol) of 4,4'-bis[(4-chlorobenzoyl)phenoxy]diphenylsulfone, 1.57 g (2.4 mmol) of bis(triphenylphosphine)nickel dichloride, 1.56 g (10.4 mmol) of sodium iodide, 8.39 g (32 mmol) of triphenylphosphine and 12.6 g (192 mmol) of zinc were measured out in a flask. The air in the flask was then replaced by dried nitrogen. To the content of the flask was then added 100 ml of N-methyl-2-pyrrolidone (NMP). The mixture was heated to a temperature of 70° C. where it was then stirred for polymerization reaction for 3 hours. The reaction solution was then poured into 3,000 ml of a 9:1 (by volume) mixture of methanol and concentrated hydrochloric acid. The resulting product was then solidified and precipitated. The result-

TABLE 1

| Example No. | Amount of sulfonic acid group (mg equivalent/g) | Tensile strength | | | | Flexing resistance | Proton conductivity | Thermal properties | |
|---|---|---|---|---|---|---|---|---|---|
| | | Elastic modulus (GPa) | Yield strength (MPa) | Breaking strength (MPa) | Elongation (%) | | | Thermal decomposition temperature (° C.) | Glass transition temperature (° C.) |
| Example 1 | 1.91 | 1.96 | 51 | 42 | 13 | Good | 0.14 | 300 | >250 |
| Example 2 | 2.62 | 1.41 | 50 | 46 | 10 | Good | 0.18 | 250 | >250 |
| Comparative Example 1 | 2.45 | 2.50 | No yield | 33 | 3 | Poor | 0.20 | 190 | >250 |

EXAMPLE 4
Preparation of 4,4'-bis[(4-chlorobenzoyl)phenoxy] diphenylsulfone (BCPES)

25.0 g (100 mmol) of 4,4'-dichlorodiphenylsulfone (Bis-S) was measured out in a 1 l three-necked flask equipped with an agitator, a Dear-Stark tube, a condenser, a three-way cock and a thermometer. The air in the flask was replaced by dried nitrogen. To the content of the flask were then added 150 ml of N,N-dimethylacetamide and 75 ml of toluene. The mixture was then stirred for dissolution. To the solution was then added 30.4 g (220 mmol) of potassium carbonate. The reaction solution was then heated to a temperature of 130° C. under reflux over an oil bath. While the resulting water was being boiled together with toluene and removed to the exterior through the Dean-Stark trap, the reaction temperature was then gradually raised to 150° C. After about 1 hour, when most of toluene was removed, the reaction solution was then cooled to a temperature of from 80° C. to 90° C. Subsequently, to the reaction solution was added 58.7 g (250 mmol) of 4-chloro-4'-fluorobenzophenone. The reaction solution was then reacted at a temperature of from 140° C. to 150° C. for 7 hours.

Figure 9:
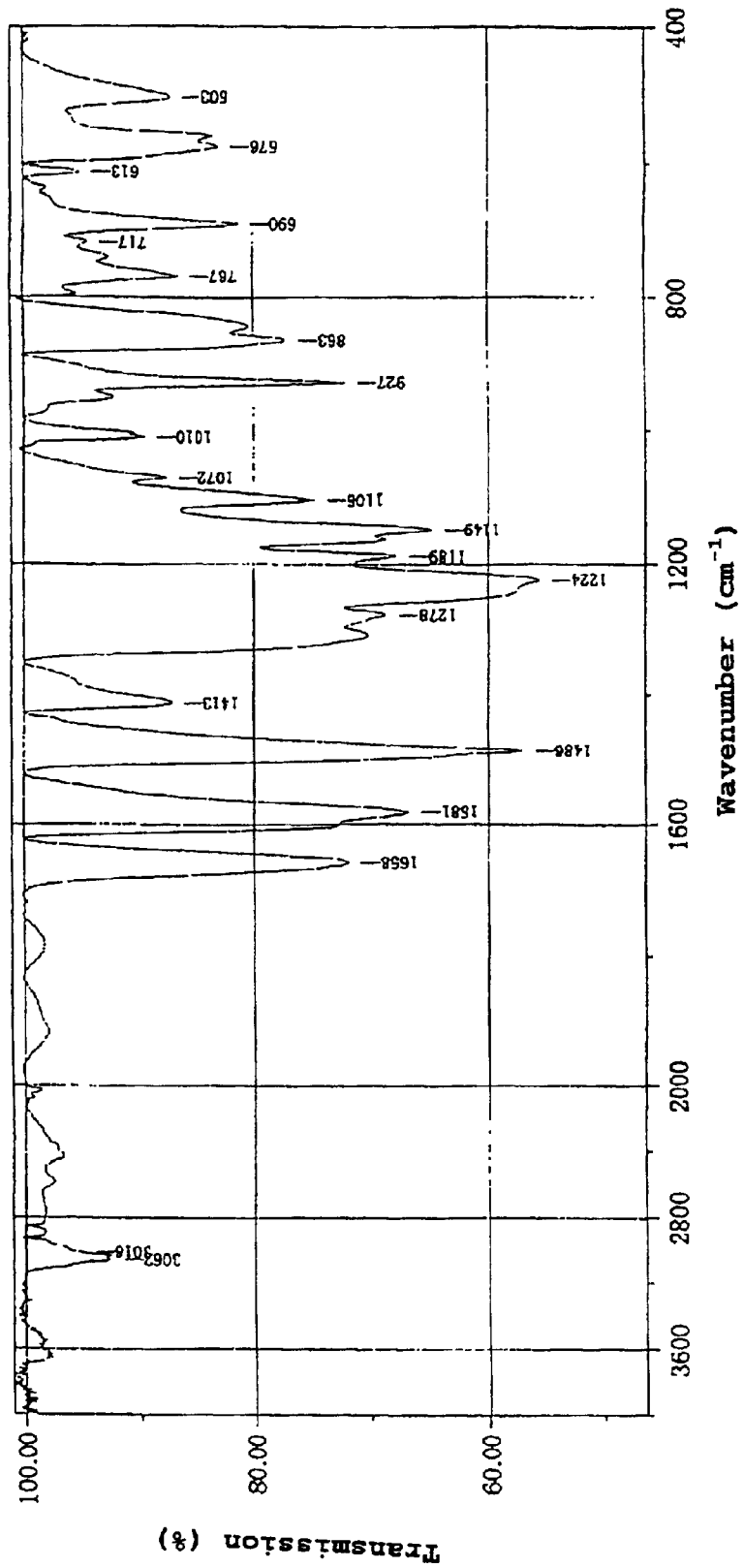
FIG. 9 is an IR spectrum of the copolymer obtained in Example 5.

After the reaction solution was allowed to cool, the inorganic materials were then removed by filtration. The filtrate was then poured into 500 ml of methanol. The resulting precipitate was withdrawn by filtration, washed with methanol, and then dried. 66 g of the resulting crude ing precipitate was withdrawn by filtration, washed with methanol, and then dried in vacuo to obtain 35 g (95%) of the desired copolymer. The IR spectrum of the copolymer thus obtained is shown in FIG. 9. The number-average molecular weight and weight-average molecular weight of the copolymer determined by GPC were 29,400 and 60,500, respectively. The copolymer exhibited a glass transition temperature of 168° C. and a thermal decomposition starting temperature of 336° C. in a nitrogen atmosphere. The film prepared from the copolymer exhibited an elastic modulus of 2.6 GPa, a yield stress of 94 MPa, a yield elongation of 6%, a tensile strength of 87 MPa and an elongation at break of 10%, demonstrating that it is ductile.

Figure 10:
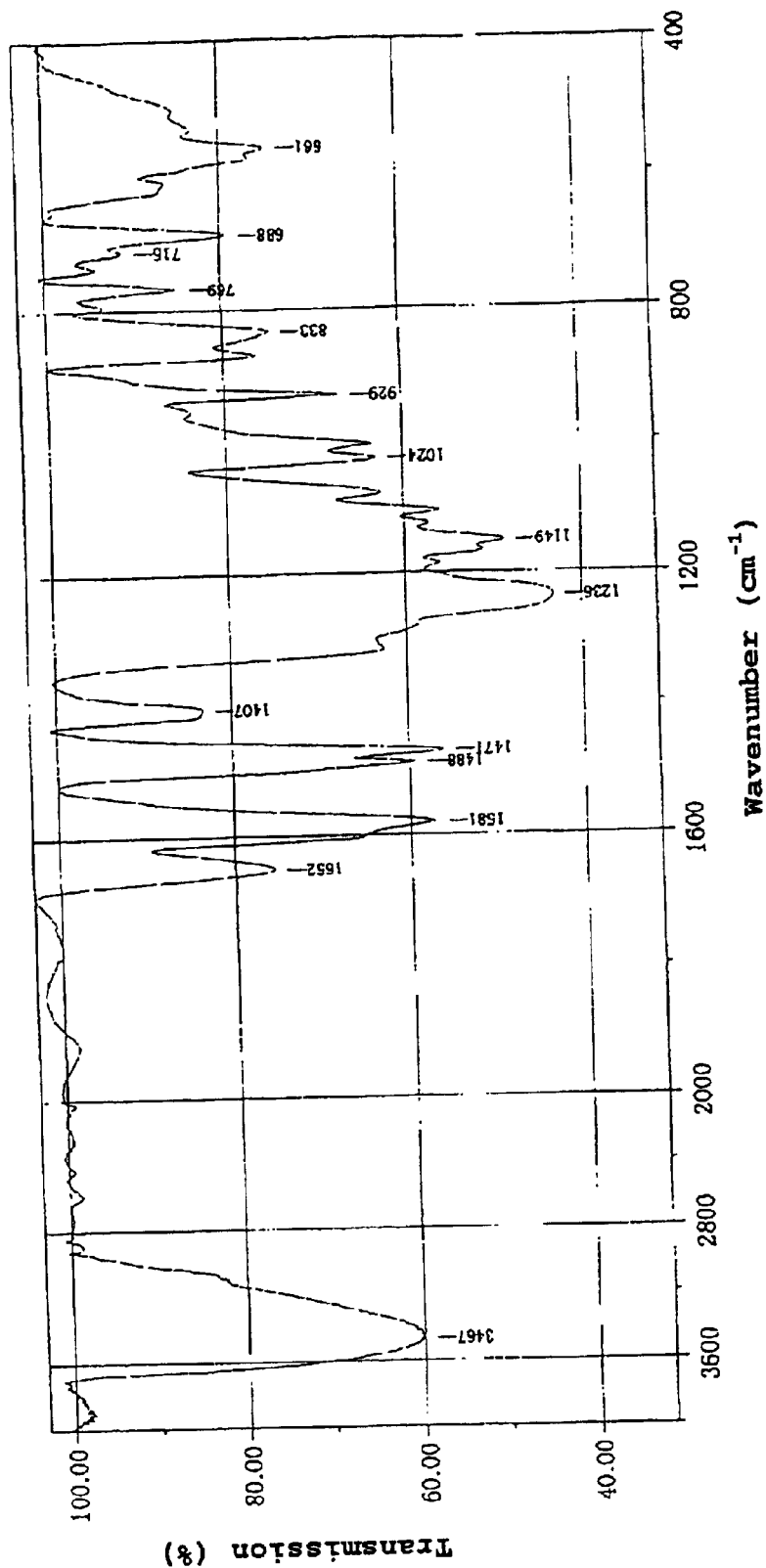
FIG. 10 is an IR spectrum of the sulfonated copolymer obtained in Example 5.

(2) Preparation of 60:40 copolymer of 2,5-dichloro-4'-(4-phenoxy)phenoxybenzophenone and 4,4'-bis[(4-chlorobenzoyl)phenoxy]diphenylsulfone To 20 g of the copolymer thus obtained was added 200 ml of concentrated sulfuric acid. The mixture was then stirred at a temperature of 60° C. for 5 hours. The reaction solution was then poured into water so that the polymer was precipitated. The polymer was repeatedly washed with water until the pH value of the wash water reached 5. The polymer was then dried to obtain 25 g (96%) of a sulfonated polymer. The infrared absorption spectrum of the sulfonated polymer is shown in FIG. 10.

The characteristics of the sulfonated polymer thus obtained are set forth in Table 2.

EXAMPLE 6

Figure 11:
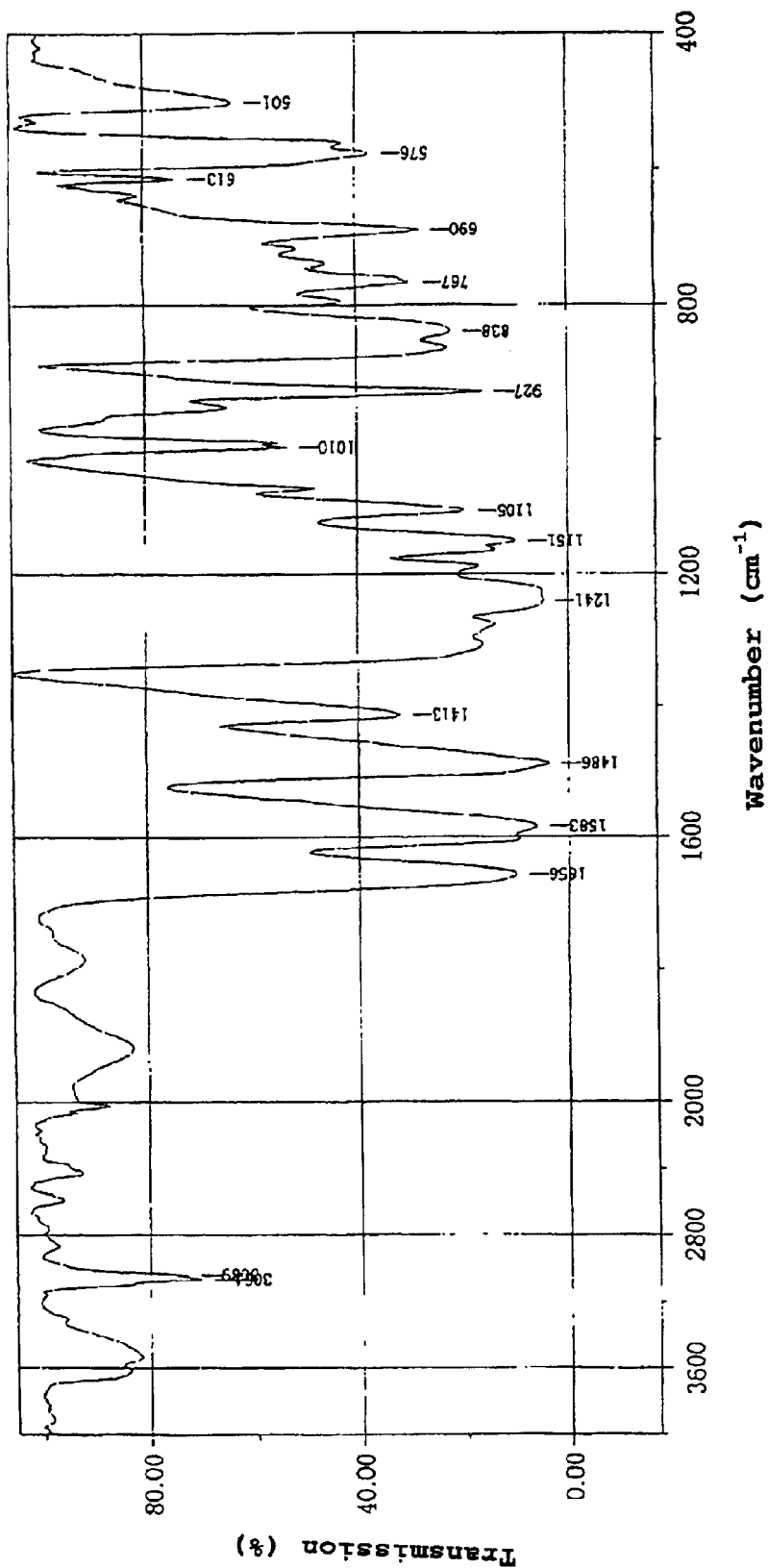
FIG. 11 is an IR spectrum of the copolymer obtained in Example 6.

(1) Preparation of 50:50 copolymer of 2,5-dichloro-4'-(4-phenoxy)phenoxybenzophenone and 4,4'-bis[(4-chlorobenzoyl)phenoxy]diphenylsulfone 15.2 g (35 mmol) of 2,5-dichloro-4'-(4-phenoxy) phenoxybenzophenone, 22.8 g (35 mmol) of 4,4'-bis[(4-chlorobenzoyl)phenoxy]diphenylsulfone, 1.37 g (2.1 mmol) of bis(triphenylphosphine)nickel dichloride, 1.36 g (9.1 mmol) of sodium iodide, 7.34 g (28 mmol) of triphenylphosphine and 110 g (168 mmol) of zinc were measured out in a flask. The air in the flask was then replaced by dried nitrogen. To the content of the flask was then added 88 ml of N-methyl-2-pyrrolidone (NMP). The mixture was heated to a temperature of 70° C. where it was then stirred for polymerization reaction for 3 hours. The reaction solution was then poured into 3,000 ml of a 9:1 (by volume) mixture of methanol and concentrated hydrochloric acid. The resulting product was then solidified and precipitated. The resulting precipitate was withdrawn by filtration, washed with methanol, and then dried in vacuo to obtain 32 g (95%) of the desired copolymer. The IR spectrum of the copolymer thus obtained is shown in FIG. 11. The number average molecular weight and weight-average molecular weight of the copolymer determined by GPC were 29,400 and 60,500, respectively. The copolymer exhibited a glass transition temperature of 168° C. and a thermal decomposition starting temperature of 336° C. in a nitrogen atmosphere. The film prepared from the copolymer exhibited an elastic modulus of 2.6 GPa, a yield stress of 94 MPa, a yield elongation of 6%, a tensile strength of 87 MPa and an elongation at break of 10%, demonstrating that it is ductile.

Figure 12:
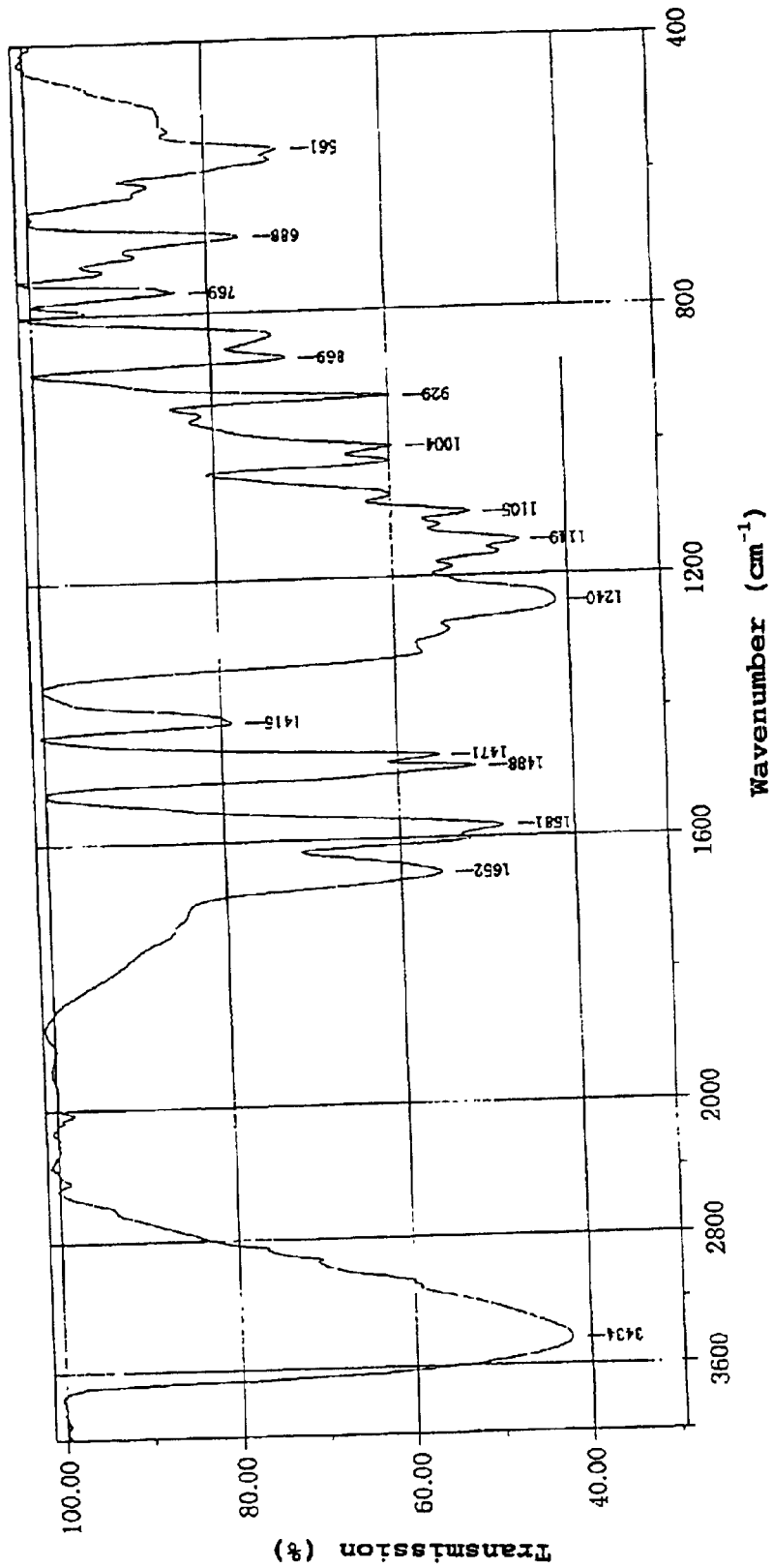
FIG. 12 is an IR spectrum of the sulfonated copolymer obtained in Example 6.

(2) Preparation of 50:50 copolymer of 2,5-dichloro-4'-(4-phenoxy)phenoxybenzophenone and 4,4'-bis[(4-chlorobenzoyl)phenoxy]diphenylsulfone To 20 g of the copolymer thus obtained was added 200 ml of concentrated sulfuric acid. The mixture was then stirred at a temperature of 60° C. for 5 hours. The reaction solution was then poured into water so that the polymer was precipitated. The polymer was repeatedly washed with water until the pH value of the wash water reached 5. The polymer was then dried to obtain 25 g (96%) of a sulfonated polymer. The infrared absorption spectrum of the sulfonated polymer is shown in FIG. 12.

The characteristics of the sulfonated polymer thus obtained are set forth in Table 2.

EXAMPLE 7

(1) The polymerization reaction procedure of Example 2 was followed except that the amount of 2,5-dichloro-4'-(4-phenoxy)phenoxybenzophenone to be used was changed to 27.36 g (42 mmol), the amount of 2,2'-bis[4-(4-chlorobenzoyl)phenoxy]diphenyl-1,1,1,3,3,3-hexafluoropropane to be used was changed to 10.68 g (14 mmol), and 3.51 g (14 mmol) of 4,4'-dichlorobenzophenone was further added. As a result, 34.2 g (94%) of a copolymer was obtained.

Figure 13:
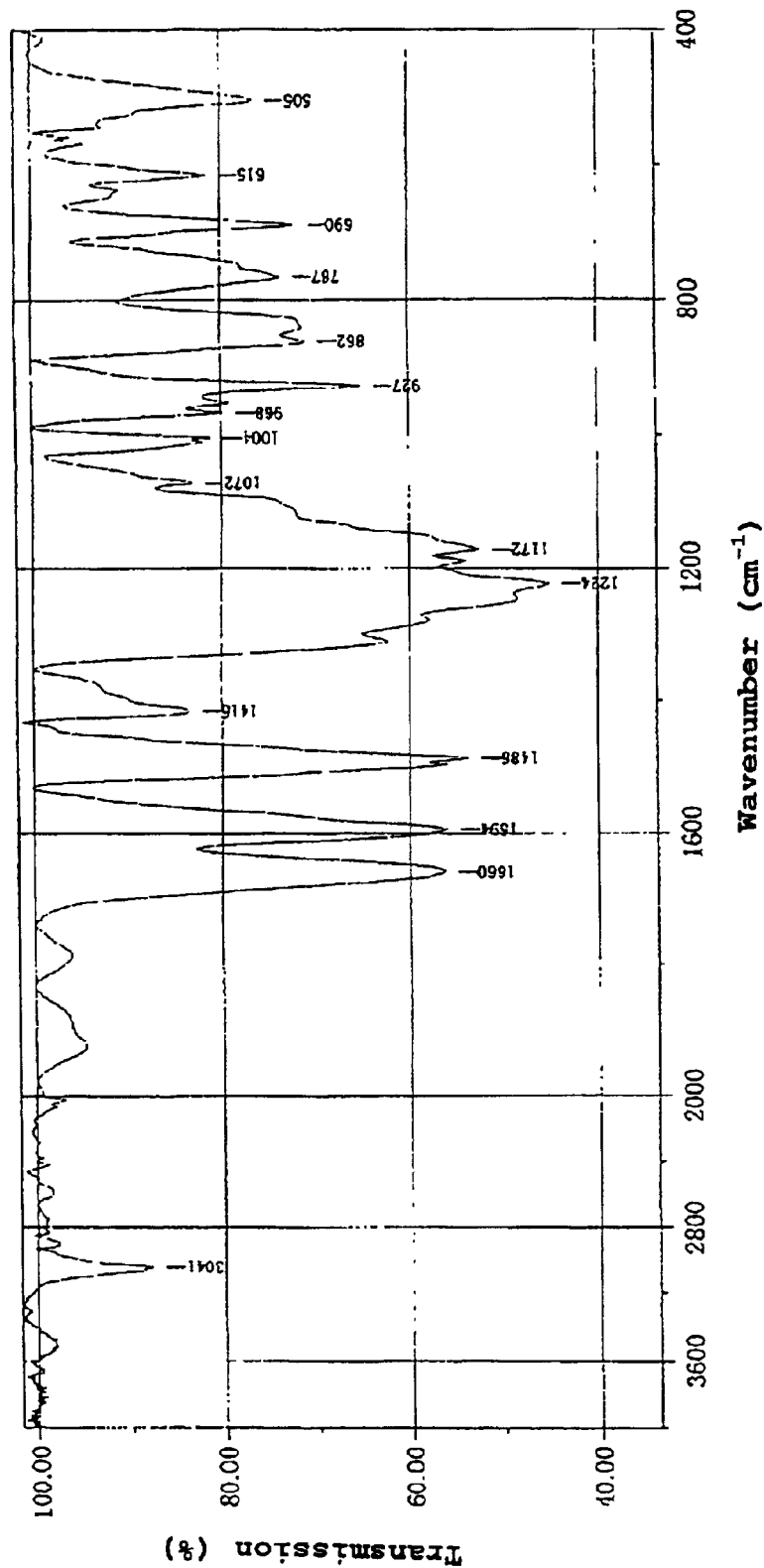
FIG. 13 is an IR spectrum of the copolymer obtained in Example 7.

The weight-average molecular weight of the polymer determined by GPC was 109,800. The infrared absorption spectrum of the polymer is shown in FIG. 13.

Figure 14:
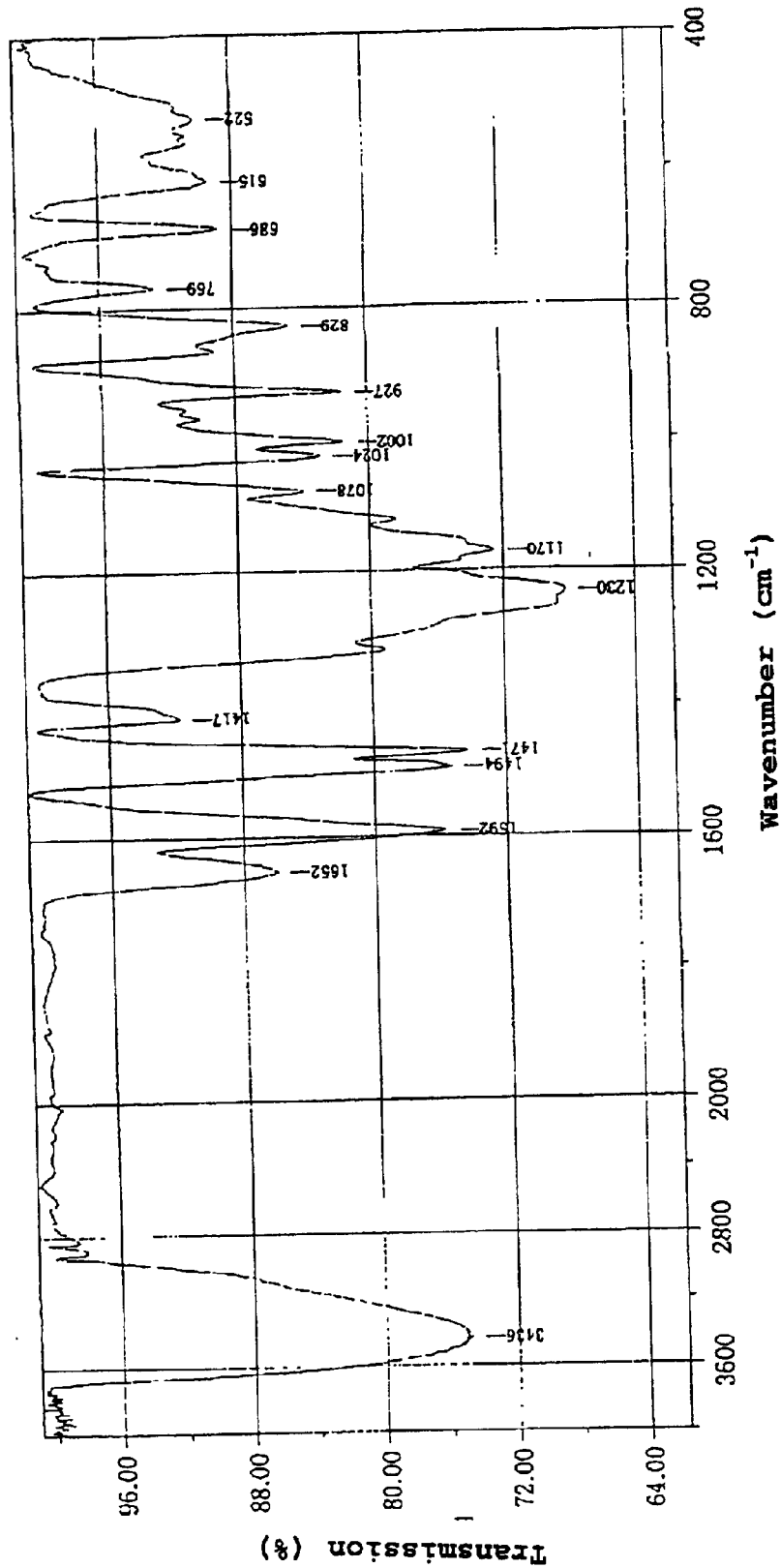
FIG. 14 is an IR spectrum of the sulfonated copolymer obtained in Example 7.

(2) To 20 g of the copolymer thus obtained was then added 200 ml of concentrated sulfuric acid. The mixture was then stirred at a temperature of 60° C. for 5 hours. The reaction solution was then poured into water so that the polymer was precipitated. The polymer was then repeatedly washed with water until the pH value of the wash water reached 5. The polymer was then dried to obtain 25 g (96%) of a sulfonated polymer. The infrared absorption spectrum of the sulfonated polymer is shown in FIG. 14.

The characteristics of the sulfonated polymer thus obtained are set forth in Table 2.

TABLE 2

| | | Tensile strength | | | | | | Thermal properties | | |
| --- | --- | --- | --- | --- | --- | --- | --- | --- | --- | --- |
| Example No. | Amount of sulfonic acid group (mg equivalent/g) | Elastic modulus (GPa) | Yield strength (MPa) | Breaking strength (MPa) | Elongation (%) | Flexing resistance | Proton conductivity | Thermal decomposition temperature (° C.) | Glass transition temperature (° C.) | Hot water resistance |
| Example 5 | 2.05 | 1.29 | 46 | 39 | 17 | Good | 0.16 | 240 | >200 | Good |
| Example 6 | 1.77 | 1.44 | 60 | 58 | 36 | Good | 0.11 | 250 | >200 | Good |
| Example 7 | 2.09 | 1.76 | 45 | 41 | 14 | Good | 0.18 | 250 | >200 | Good |

EXAMPLE 8

Synthesis of oligomer 67.3 g (0.20 mols) of 2,2-bis(4-hydroxyphenyl)-1,1,1,3,3,3-hexafluoropropoane (bisphenol AF), 60.3 g (0.24 mols) of 4,4'-dichlorobenzenephenone (4,4'-DCBP), 71.9 g (0.52 mols) of potassium carbonate, 300 ml of N,N-dimethylacetamide (DMAc) and 150 ml of toluene were measured out in all three-necked flask equipped with an agitator, a thermometer, a condenser, a Dean-Stark tube and a three-way cock for introducing nitrogen. The reaction mixture was then reacted at a temperature of 130° C. with stirring in a nitrogen atmosphere over an oil bath. While the resulting water was being boiled together with toluene and removed through the Dean-Stark tube, the reaction occurred. As a result, little or no production of water was observed in about 3 hours. The reaction temperature was then gradually raised from 130° C. to 150° C. Thereafter, most of toluene was removed while the reaction temperature was being gradually raised to 150° C. The reaction continued at a temperature of 150° C. for 10 hours. To the reaction solution was then added 10.0 g (0.40 mols) of 4,4'-DCBP. The reaction then continued for 5 hours. The resulting reaction solution was then allowed to cool. The resulting inorganic compound precipitate was then removed by filtration. The resulting filtrate was then put in 4 liters of methanol. The product thus precipitated was withdrawn by filtration, recovered, dried, and then dissolved in 300 ml of tetrahydrofurane. The product was then reprecipitated in 4 l of methanol to obtain 95 g (yield: 85%) of the desired compound.

Figure 15:
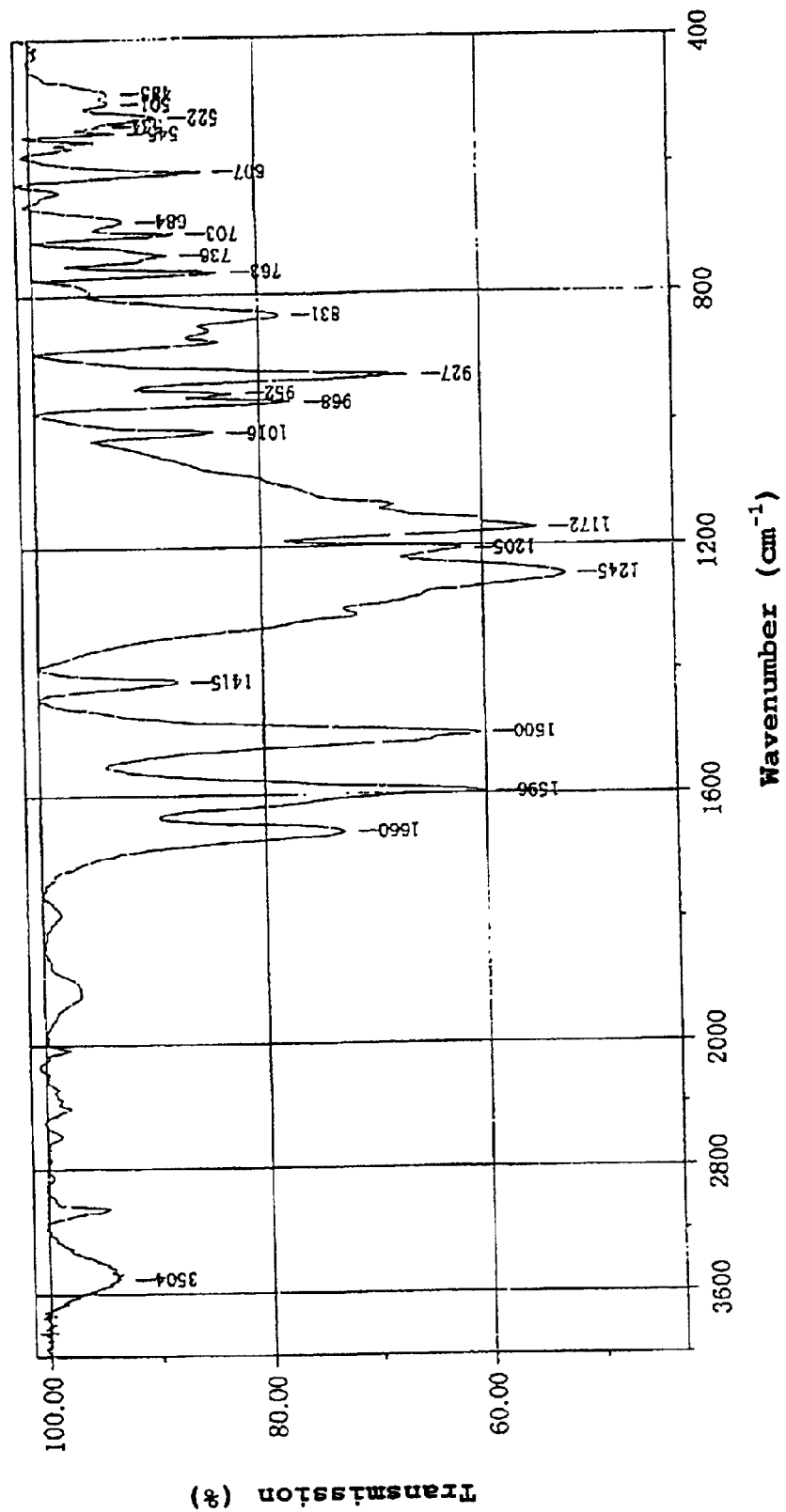
FIG. 15 is an IR spectrum of the oligomer as a halogenated aromatic compound of the invention obtained in Example 8.

The number average molecular weight and weight-average molecular weight of the polymer by GPC (solvent: THF) in polystyrene equivalence were 4,200 and 8,300, respectively. The infrared absorption spectrum of the polymer thus obtained is shown in FIG. 15. The polymer thus obtained was soluble in THF, NMP, DMAc, sulfolane, etc. and exhibited Tg of 110° C. and a thermal decomposition temperature of 498° C.

It is presumed that the polymer thus obtained has a structure represented by the following general formula (7):

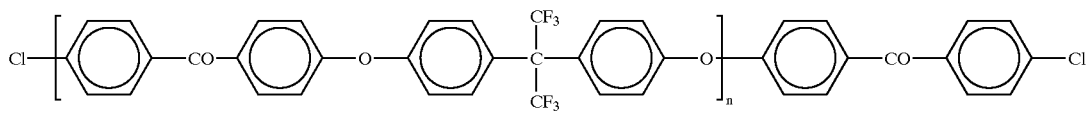

(7)

From the foregoing structure and the foregoing number average molecular weight, the average value of n was determined to be 7.8.

EXAMPLE 9
Synthesis of oligomer

The polymerization procedure of Example 8 was followed except that the amount of bisphenol AF and 4,4'-DCBP to be initially charged as monomers were changed to 67.3 g (0.20 mols) and 58.3 g (0.232 mols), respectively, and the amount of 4,4'-DCBP to be later charged was changed to 2 g (0.029 mols). As a result, a polymer was obtained in a yield of 88% and an amount of 71 g. The number-average molecular weight and weight average molecular weight of the polymer determined by GPC (solvent: THF) in polystyrene equivalence were 7,300 and 16,400, 16,400, respectively. The polymer thus obtained was soluble in THF, NMP, DMAc, sulfolane, etc. and exhibited Tg of 129° C. and a thermal decomposition temperature of 516° C. The polymer thus obtained is represented by the general formula (7) wherein n is 13.9 (average value).

EXAMPLE 10
Synthesis of oligomer

The polymerization procedure of Example 8 was followed except that the amount of bisphenol AF and 4,4'-DCBP to be initially charged as monomers were changed to 67.3 g (0.20 mols) and 53.5 g (0.214 mols), respectively, and the amount of 4,4'-DCBP and potassium carbonate to be later charged were changed to 3.3 g (0.0133 mols) and 34.6 g (0.251 mols), respectively. As a result, a polymer was obtained in a yield of 93% and an amount of 98 g.

The number average molecular weight and weight-average molecular weight of the polymer determined by GPC (solvent: THF) in polystyrene equivalence were 9,900 and 22,000, respectively. The polymer thus obtained was soluble in THF, NMP, DMAc, sulfolane, etc. and exhibited Tg of 151° C. and a thermal decomposition temperature of 524° C. The polymer thus obtained is represented by the general formula (7) wherein n is 18.9 (average value).

EXAMPLE 11
Synthesis of oligomer 67.3 g (0.20 mols) of bisphenol AF, 50.2 g (0.20 mols) of 4,4'-DCBP, 71.9 g (0.52 mols) of potassium carbonate, 300 ml of sulfolane and 150 ml of toluene were measured out in a 1 l three-necked flask equipped with an agitator, a thermometer, a condenser, a Dean-Stark tube and a three-way cock for introducing nitrogen. The reaction mixture was then reacted at a temperature of 130° C. with stirring in a nitrogen atmosphere over an oil bath. While the resulting water was being boiled together with toluene and removed through the Dean-Stark tube, the reaction occurred. As a result, no production of water was observed in about 3 hours. The reaction temperature was then gradually raised from 130° C. to 160° C. Thereafter, most of toluene was removed while the reaction temperature was being gradually raised to 180° C. The reaction continued at a temperature of 180° C. for 16 hours. To the reaction solution was then added 10.0 g (0.40 mols) of 4,4'-DCBP. The reaction then continued for 4 hours. The resulting reaction solution was then allowed to cool. The resulting inorganic compound precipitate was then removed by filtration. The resulting filtrate was then put in 4 l of methanol. The product thus precipitated was withdrawn by filtration, recovered, dried, and then dissolved in 300 ml of THF. The product was then reprecipitated in 4 l of methanol to obtain 82.5 g (yield: 80.2%) of the desired compound.

The number average molecular weight and weight-average molecular weight of the polymer by GPC (solvent: THF) in polystyrene equivalence were 16,400 and 37,400, respectively. The polymer thus obtained was soluble in THF, NMP, DMAc, sulfolane, etc. and exhibited Tg of 162° C. and a thermal decomposition temperature of 535° C. The polymer thus obtained is represented by the general formula (7) wherein n is 31.6 (average value).

EXAMPLE 12

The polymerization procedure of Example 8 was followed except that 4,4'-DCBP was replaced by bis(4-chlorophenyl) sulfone (BCPS) which was initially charged in an amount of 53.5 g (0.214 mols) and later charged in an amount of 3.3 g (0.0133 mols) and the amount of potassium carbonate to be used was changed to 58.0 g (0.42 mols). As a result, a polymer was obtained in a yield of 96% and an amount of 120 g.

Figure 16:
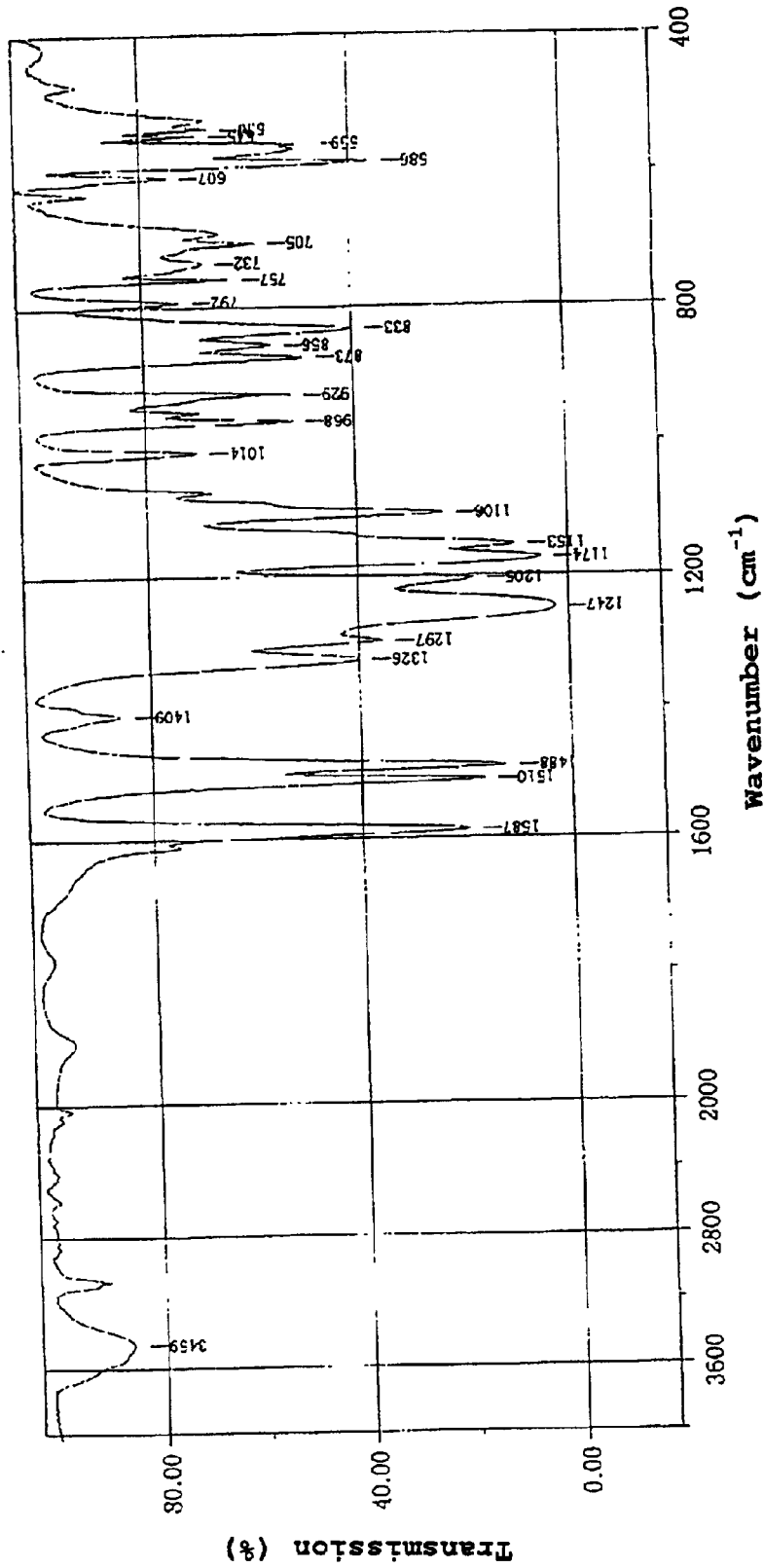
FIG. 16 is an IR spectrum of the oligomer as a halogenated aromatic compound of the invention obtained in Example 12.

The number average molecular weight and weight-average molecular weight of the polymer in polystyrene equivalence determined by GPC (solvent: THF) were 4,600 and 7,600, respectively. The infrared absorption spectrum of the polymer is shown in FIG. 16. The polymer thus obtained was soluble in THF, NMP, DMAc, sulfolane, etc. and exhibited Tg of 158° C. and a thermal decomposition temperature of 513° C.

It is presumed that the polymer thus obtained has a structure represented by the following general formula (8):

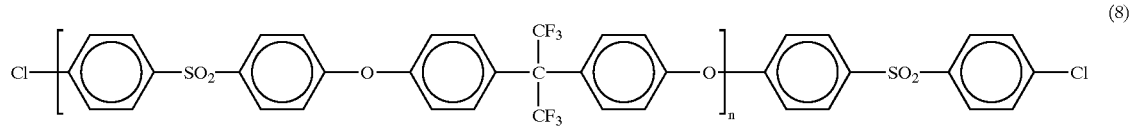

(8)

According to the same method as used in Example 8, n was determined to be 8.0 on the average.

EXAMPLE 13

Figure 17:
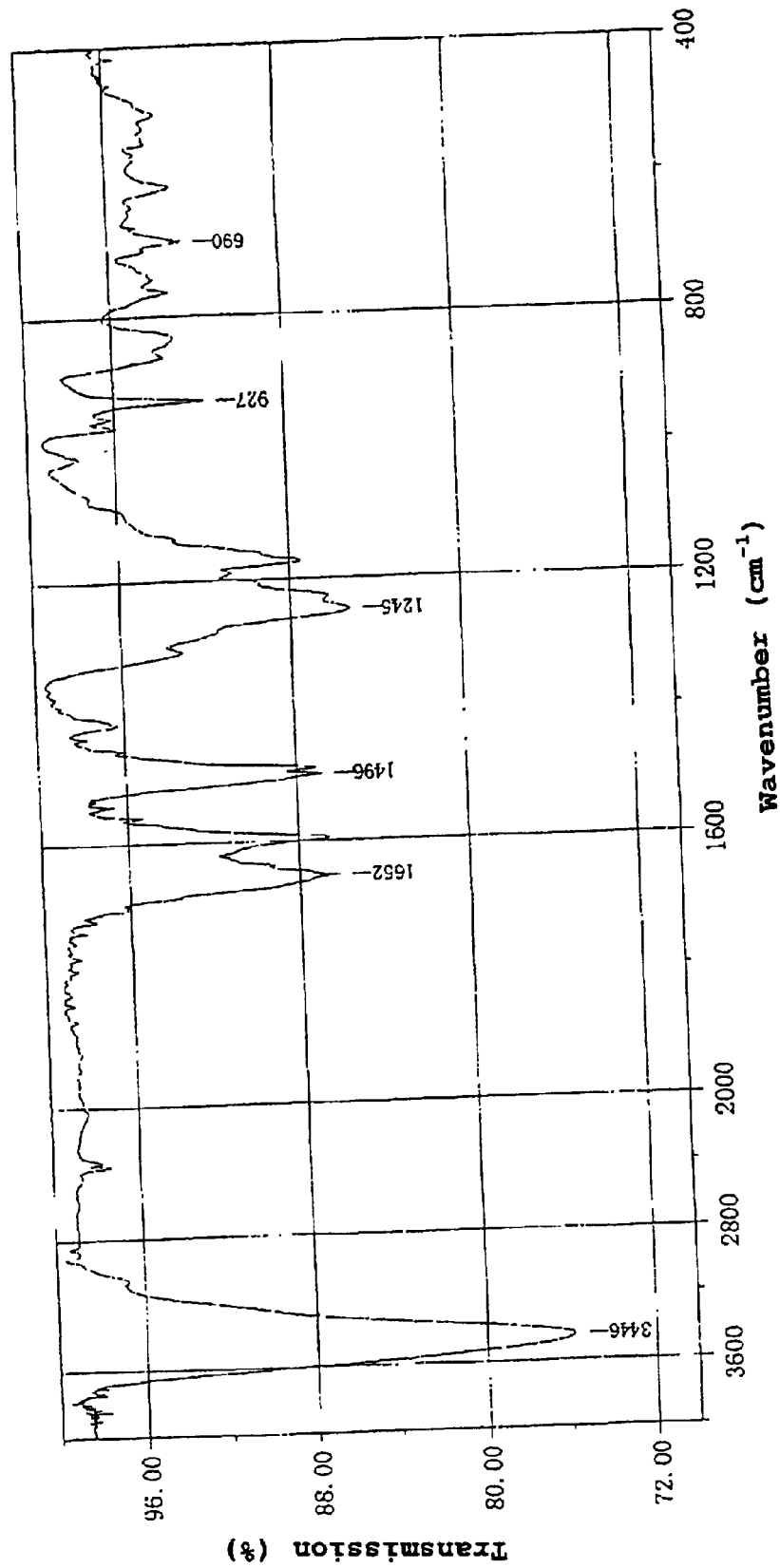
FIG. 17 is an IR spectrum of the copolymer obtained in the step (1) of Example 13.

(1) Synthesis of polymer 28.4 g (2.87 mmol) of the oligomer obtained in Example 10, 29.2 g (67.1 mmol) of 2,5-dichloro-4'-(4-phenoxy) phenoxybenzophenone (DCPPB), 1.37 g (2.1 mmol) of bis(triphenylphosphine)nickel dichloride, 1.36 g (9.07 mmol) of sodium iodide, 7.34 g (28.0 mmol) of triphenyl phosphine, and 11.0 g (168 mmol) of zinc powder were measured out in a flask. The air in the flask was then replaced by dried nitrogen. To the content of the flask was then added 130 ml of N-methyl-2-pyrrolidone. The mixture was heated to a temperature of 80° C. where it was then stirred for polymerization for 4 hours. The polymerization solution was then diluted with THF. The polymerization solution thus diluted was then treated with a mixture of hydrochloric acid and methanol to undergo solidification. The solid matter was repeatedly washed with methanol, and then dissolved in THF. The solution was then reprecipitated in methanol so that it was purified. The polymer was collected by filtration, and then dried in vacuo to obtain 50.7 g (96%) of the desired copolymer. The number average molecular weight and weight-average molecular weight of the copolymer in polystyrene equivalence determined by GPC (THF) were 40,000 and 145,000, respectively. The infrared absorption spectrum of the copolymer is shown in FIG. 17.

Figure 18:
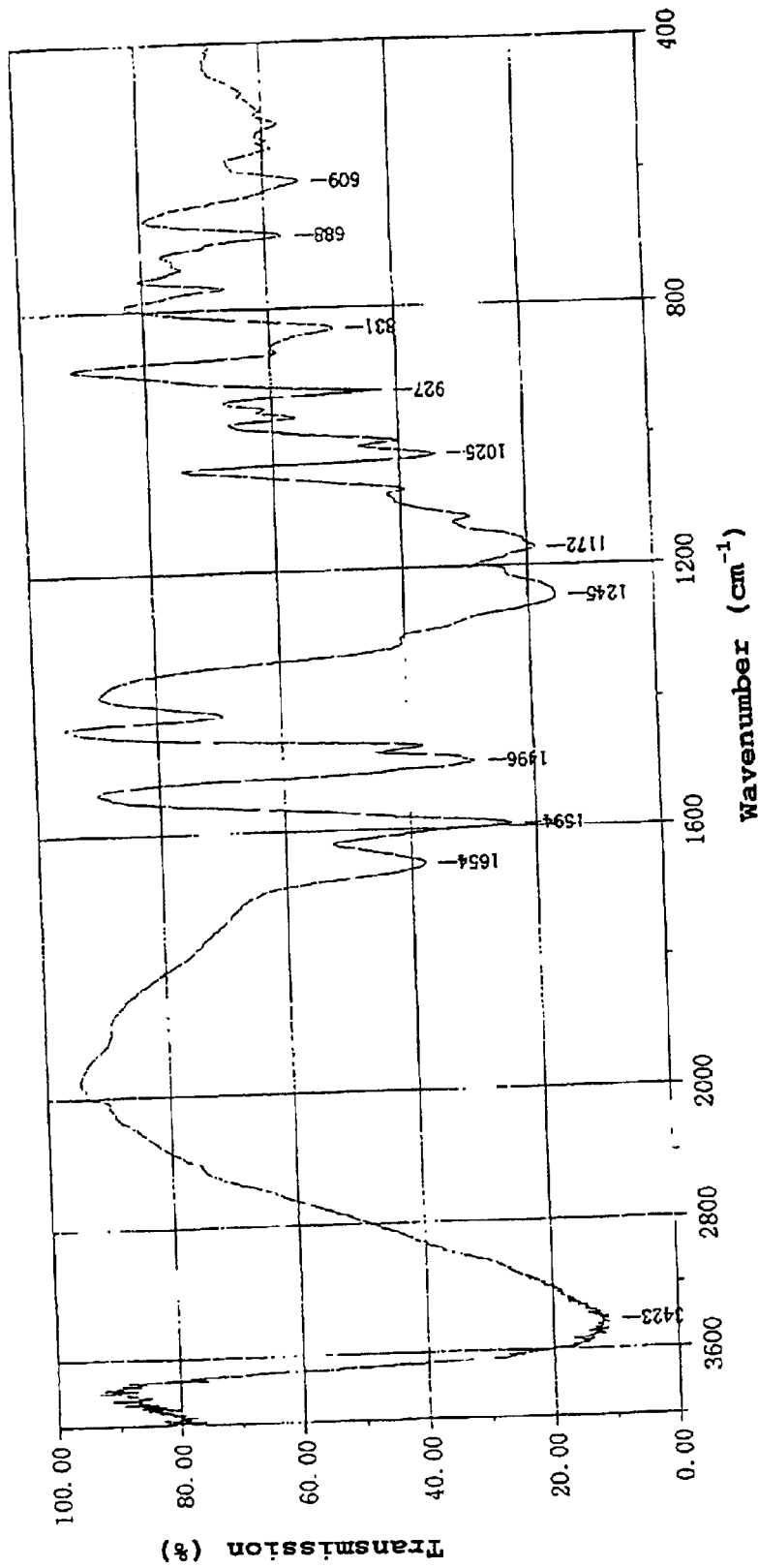
FIG. 18 is an IR spectrum of the sulfonated copolymer obtained in the step (2) of Example 13.

(2) Preparation of sulfonated polymer 25 g of the copolymer obtained in the step (1) was put in a 500 ml separable flask. To the content of the flask was then added 250 ml of a 96% sulfuric acid. The solution thus obtained was then poured into a large amount of ion-exchanged water so that the polymer was precipitated. The polymer was then washed with water until the pH value of the wash water reached 5. The polymer was then dried to obtain 29 g (96%) of a sulfonated polymer. The infrared absorption spectrum of the sulfonated polymer is shown in FIG. 18.

The sulfonated polymer thus obtained was dissolved in NMP to obtain a solution which was then casted to form a film. The sulfonation equivalent of the sulfonated polymer was 1.72 mg equivalent/g. The characteristics of the sulfonated polymer are set forth in Table 3.

EXAMPLE 14

(1) Synthesis of polymer 13.8 g of the oligomer obtained in Example 12 and 11.75 g (27 mmol) of DCPPB as monomers and 0.589 g (0.9 mmol) of bis(triphenylphosphine)nickel chloride, 0.585 g (3.9 mmol) of sodium iodide, 3.148 g (12 mmol) of triphenyl phosphine, and 4.701 g (72 mmol) of zinc powder were put in a three-necked flask equipped with a reflux condenser and a three-way cock. The air in the flask was then replaced by nitrogen three times over a 70° C. oil bath. The flask was then allowed to stand under reduced pressure for 1 hour. Thereafter, the atmosphere of the reaction system was returned to nitrogen. To the reaction solution was then added 60 ml of N-methyl-2-pyrrolidone. The reaction solution was then subjected to polymerization at a temperature of 80° C. After 10 hours of reaction, the reaction product was then diluted with 50 ml of N-methyl-2-pyrrolidone. The reaction product was then reprecipitated in a 1:10 mixture of hydrochloric acid and methanol to cause the precipitation of a polymer in the form of a white powder. The polymer was recovered, and then dried at a temperature of 60° C. in vacuo.

Figure 19:
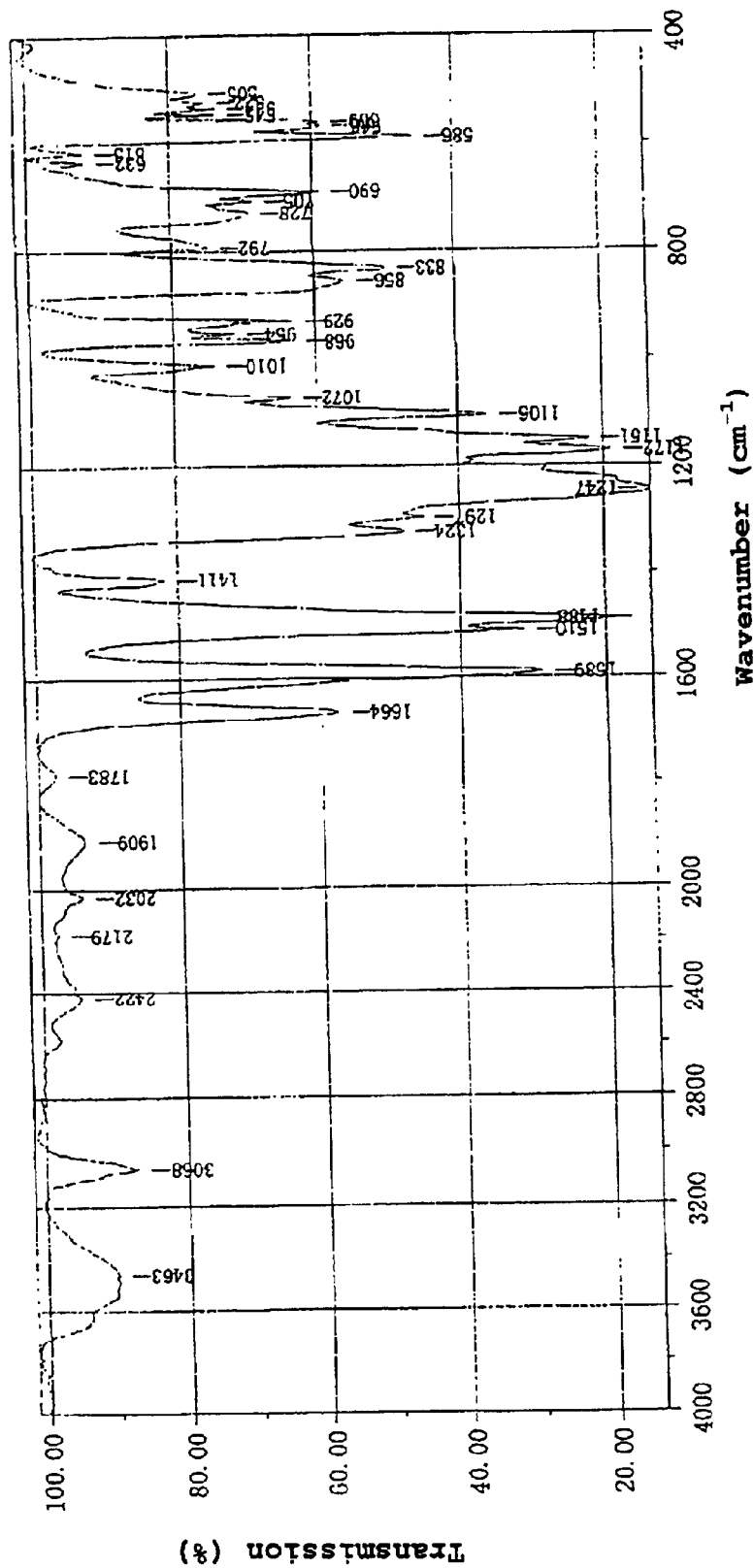
FIG. 19 is an IR spectrum of the copolymer obtained in the step (1) of Example 14.

The yield was 22.5 g (96%). The number average molecular weight and weight-average molecular weight of the polymer in polystyrene equivalence determined by GPC (THF) were 33,000 and 138,000, respectively. The infrared absorption spectrum of the polymer is shown in FIG. 19.

(2) Preparation of sulfonated polymer

Figure 20:
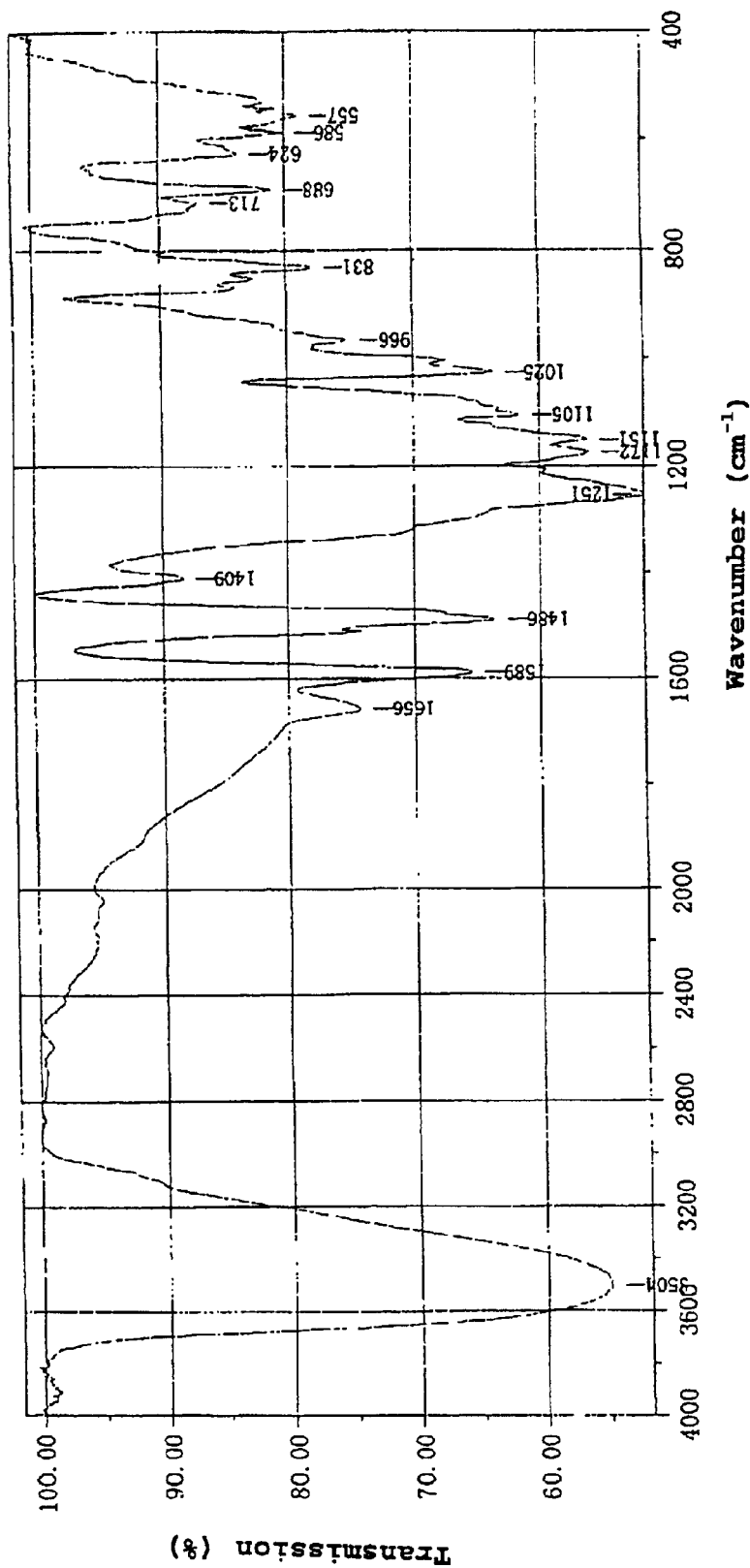
FIG. 20 is an IR spectrum of the sulfonated copolymer obtained in the step (2) of Example 14.

To 25 g of the polymer obtained in the step (1) was then added 250 ml of concentrated sulfuric acid. In a nitrogen atmosphere, the reaction mixture was then stirred at room temperature for 24 hours to undergo sulfonation. The reaction product was then reprecipitated in purified water so that the sulfonated polymer was precipitated. The water was exchanged several times. Thus, the polymer was washed until the pH value of the wash water reached 5. The sulfonated polymer thus obtained was recovered, and then dried over 80° C. hot air. The yield of the sulfonated polymer was 29 g (95%). The infrared absorption spectrum of the sulfonated polymer is shown in FIG. 20. The sulfonated polymer thus obtained was dissolved in NMP to obtain a solution which was then casted to form a film. The sulfonation equivalent of the sulfonated polymer was 1.95 mg equivalent/g. The characteristics of the sulfonated polymer are set forth in Table 3.

TABLE 3

| | Tensile strength | | | | | | Thermal properties | |
|---|---|---|---|---|---|---|---|---|
| Example No. | Elastic modulus (GPa) | Yield strength (MPa) | Breaking strength (MPa) | elongation (%) | Flexing resistance | Proton conductivity | Thermal decomposition temperature (° C.) | Glass transition temperature (° C.) |
| Example 13 | 1.87 | 2.05 | 48 | 35 | Good | 0.22 | 300 | >250 |
| Example 14 | 2.02 | 1.87 | 45 | 24 | Good | 0.18 | 300 | >250 |

The halogenated aromatic compound of the invention is useful for the incorporation of a flexible structure in the molecule of a polymer. The aromatic polymer thus obtained has a flexible structure incorporated in the main chain and thus exhibits a high toughness. Thus, even when subjected to sulfonation, the aromatic polymer can hardly be deteriorated in its mechanical properties and thermal properties. The sulfonic acid group-containing polymer obtained by the sulfonation of the polymer can be used as a proton-conductive membrane material. The proton-conductive membrane thus obtained is excellent in mechanical strength and durability.

A preferred embodiment of the copolymer having a repeating unit represented by the general formula (2) allows easy control over the amount of sulfonic acid group during the sulfonation. The sulfonic acid group-containing copolymer thus obtained acts as a conductive membrane which exhibits a high proton conductivity over a wide temperature range, an excellent adhesion to the substrate and electrode, no brittleness and hence an excellent strength and an excellent tepid water resistance.

Accordingly, the proton-conductive membrane of the invention can be used as a proton-conductive membrane for primary battery electrolyte, secondary battery electrolyte, fuel cell polymer solid electrolyte, display element, various sensors, signal transfer medium, solid capacitor, ion exchange membrane, etc. and thus has an extremely great industrial significance.

While the invention has been described in detail and with reference to specific embodiments thereof, it will be apparent to one skilled in the art that various changes and modifications can be made therein without departing from the spirit and scope thereof.

What is claimed is:

1. A polyphenylene polymer having a repeating unit represented by the following general formula (1):

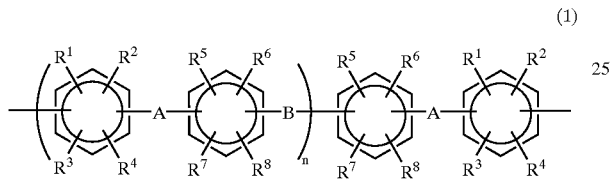

(1)

wherein A independently represents an electron-withdrawing group; B independently represents an electron-donating atom or group; $R^1$ to $R^8$ may be the same or different and each represent a hydrogen atom, fluorine atom or alkyl group; and n represents an integer of not smaller than 2, wherein said polyphenylene polymer has a weight average molecular weight of from 10,000 to 1,000,000 in polystyrene equivalence.

2. The polyphenylene polymer according to claim 1, which is a copolymer having a repeating unit comprising a divalent aromatic group other than the repeating unit represented by the general formula (1).

3. The polyphenylene polymer according to claim 2, wherein said repeating unit comprising a divalent aromatic group is at least one unit selected from the group consisting of those represented by the following general formulae (2) to (5):

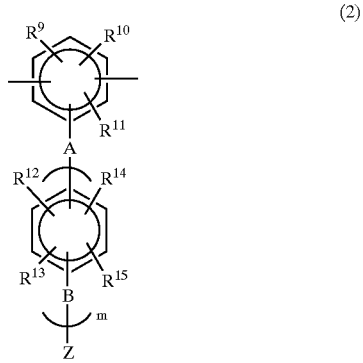

(2)

wherein A independently represents an electron-withdrawing group; B independently represents an electron-donating atom or group; $R^9$ to $R^{15}$ may be the same or different and each represent a hydrogen atom or alkyl group; Z represents an aryl group; and m represents an integer of from 0 to 2;

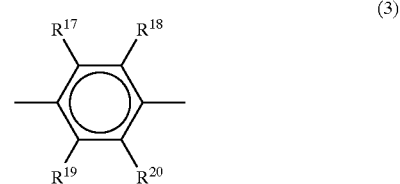

(3)

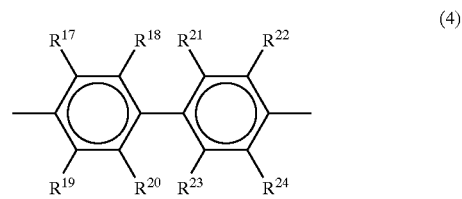

(4)

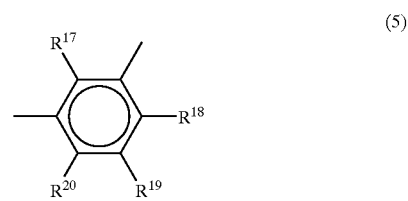

(5)

wherein $R^{17}$ to $R^{24}$ may be the same or different and each represent a hydrogen atom, fluorine atom, alkyl group or aryl group.

4. The polyphenylene polymer as claimed in claim 2 and 3, having a sulfonic acid group in its molecule.

5. The polyphenylene polymer as claimed in claim 4, containing a sulfonic acid group in an amount of from 0.5 to 3.0 mg equivalent/g.

6. A proton-conductive membrane comprising a polyphenylene polymer having a sulfonic acid group as claimed in claim 4.

7. The polyphenylene polymer according to claim 1, wherein A is an electron-withdrawing group selected from the group consisting of —CO—, —CONH—, —(CF$_2$)p—, in which p is an integer of from 1 to 10, —C(CF$_3$)$_2$—, —COO—, —SO— and —SO$^2$—.

8. The polyphenylene polymer according to claim 1, wherein A has a Hammett's substituent constant of not smaller than 0.6 or not smaller than 0.01 when located in the meta position or para position, respectively, in the phenyl group.

9. The polyphenylene polymer according to claim 1, wherein B is an electron-donating group or atom selected from the group consisting of —O—, —S—, —CH=CH—, —C≡C—,

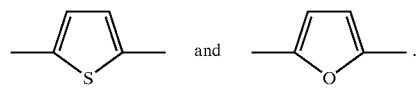

10. The polyphenylene polymer according to claim 1, comprising from 10 to 80 mol % of said repeating unit of formula (1).

* * * * *